(12) United States Patent
Hariri et al.

(10) Patent No.: US 9,925,221 B2
(45) Date of Patent: Mar. 27, 2018

(54) TREATMENT OF AMYOTROPHIC LATERAL SCLEROSIS USING PLACENTAL STEM CELLS

(75) Inventors: Robert J. Hariri, Bernardsville, NJ (US); Jodi P. Gurney, Chicago, IL (US)

(73) Assignee: Celularity, Inc. NJ (US)

( * ) Notice: Subject to any disclaimer, the term of this patent is extended or adjusted under 35 U.S.C. 154(b) by 53 days.

(21) Appl. No.: 14/343,283

(22) PCT Filed: Sep. 10, 2012

(86) PCT No.: PCT/US2012/054493
§ 371 (c)(1),
(2), (4) Date: Oct. 27, 2014

(87) PCT Pub. No.: WO2013/055476
PCT Pub. Date: Apr. 18, 2013

(65) Prior Publication Data
US 2015/0044177 A1    Feb. 12, 2015

Related U.S. Application Data

(60) Provisional application No. 61/533,103, filed on Sep. 9, 2011.

(51) Int. Cl.
*A01N 63/00* (2006.01)
*A61K 35/50* (2015.01)
*A61K 45/06* (2006.01)

(52) U.S. Cl.
CPC .............. *A61K 35/50* (2013.01); *A61K 45/06* (2013.01)

(58) Field of Classification Search
None
See application file for complete search history.

(56) References Cited

U.S. PATENT DOCUMENTS

| | | |
|---|---|---|
| 3,862,002 A | 1/1975 | Sanders |
| 4,798,824 A | 1/1989 | Belzer et al. |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,356,373 A | 10/1994 | Dracker et al. |
| 5,372,581 A | 12/1994 | Anderson |
| 5,385,901 A | 1/1995 | Kaplan |
| 5,415,665 A | 5/1995 | Hessel et al. |
| 5,437,994 A | 8/1995 | Emerson et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,552,267 A | 9/1996 | Stern et al. |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |

(Continued)

FOREIGN PATENT DOCUMENTS

| | | |
|---|---|---|
| WO | WO 2007/079184 A2 | 7/2007 |
| WO | WO 2007/079185 A2 | 7/2007 |
| WO | WO 2009/008928 A2 | 1/2009 |

OTHER PUBLICATIONS

Kwon et al. J Neurochem 2014;131:206-18.*
Andersen and Al-Chalabi, 2011, "Clinical genetics of amyotrophic lateral sclerosis: what do we really know?", Nat Rev Neurol, 7:603-615.
Bostian and Betts, 1978, "Kinetics and reaction mechanism of potassium-activated aldehyde dehydrogenase from *Saccharomyces cerevisiae*", Biochem J, 173:787-798.

(Continued)

*Primary Examiner* — Janice Li
(74) *Attorney, Agent, or Firm* — Celularity, Inc.; Timothy L. Smith

(57) ABSTRACT

Provided herein are methods of treatment of an individual having amyotrophic lateral sclerosis, comprising administering to the individual a therapeutically effective amount of placental stem cells, e.g., tissue culture surface-adherent placental stem cells (PDACs). In one aspect, provided herein is a method of treating amyotrophic lateral sclerosis (ALS) comprising administering to an individual having ALS a therapeutically effective amount of placental stem cells. In certain embodiments, "therapeutically effective" means an amount effective to reduce or ameliorate one or more symptoms of ALS.

20 Claims, No Drawings

(56) References Cited

U.S. PATENT DOCUMENTS

| | | |
|---|---|---|
| 5,763,266 A | 6/1998 | Palsson et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,861,315 A | 1/1999 | Nakahata et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Stmb et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Varfaille et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,455,678 B1 | 9/2002 | Yin et al. |
| 6,461,615 B1 | 10/2002 | Boyse et al. |
| 6,461,645 B1 | 10/2002 | Boyse et al. |
| 6,497,875 B1 | 12/2002 | Sorrell et al. |
| 6,528,245 B2 | 3/2003 | Sanchez-Ramos et al. |
| 6,541,024 B1 | 4/2003 | Kadiyala et al. |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 7,029,666 B2 | 4/2006 | Bruder et al. |
| 7,045,148 B2 | 5/2006 | Hariri |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,875,272 B2 | 1/2011 | Messina et al. |
| 7,875,273 B2 | 1/2011 | Messina et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,021,876 B2 | 9/2011 | Atala et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 8,197,804 B2 * | 6/2012 | Sing ................. A61K 35/48 |
| | | 424/93.1 |
| 8,202,703 B2 | 6/2012 | Edinger et al. |
| 8,263,065 B2 | 9/2012 | Zhang et al. |
| 8,293,223 B2 | 10/2012 | Hariri |
| 8,545,833 B2 | 10/2013 | Hariri |
| 8,562,973 B2 | 10/2013 | Edinger |
| 8,591,883 B2 | 11/2013 | Edinger et al. |
| 8,691,217 B2 | 4/2014 | Edinger et al. |
| 8,703,927 B2 | 4/2014 | Seehra et al. |
| 8,926,964 B2 | 1/2015 | Hariri et al. |
| 8,969,315 B2 | 3/2015 | Abbot et al. |
| 9,149,569 B2 | 10/2015 | Hariri |
| 9,198,938 B2 | 12/2015 | Hariri et al. |
| 9,216,200 B2 | 12/2015 | Hariri et al. |
| 9,254,302 B2 | 2/2016 | Abbot |
| 2001/0005591 A1 | 6/2001 | Qasba et al. |
| 2002/0102239 A1 | 8/2002 | Koopmans |
| 2002/0123141 A1 | 9/2002 | Hariri |
| 2002/0132343 A1 | 9/2002 | Lum |
| 2002/0160510 A1 | 10/2002 | Hariri |
| 2003/0032179 A1 | 2/2003 | Hariri |
| 2003/0044977 A1 | 3/2003 | Sakuragawa et al. |
| 2003/0235563 A1 | 4/2003 | Strom et al. |
| 2003/0180269 A1 | 9/2003 | Hariri |
| 2003/0187515 A1 | 10/2003 | Hariri |
| 2003/0235909 A1 | 12/2003 | Hariri |
| 2004/0018617 A1 | 1/2004 | Hwang |
| 2004/0028660 A1 | 2/2004 | Hariri et al. |
| 2004/0048372 A1 | 3/2004 | Hariri |

(56) References Cited

U.S. PATENT DOCUMENTS

| | | |
|---|---|---|
| 2004/0048796 A1 | 3/2004 | Hariri et al. |
| 2004/0107453 A1 | 6/2004 | Furcht et al. |
| 2004/0161419 A1 | 6/2004 | Strom et al. |
| 2004/0136967 A1 | 7/2004 | Weiss et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118715 A1 | 6/2005 | Hariri et al. |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0008450 A1 | 1/2006 | Verfaillie et al. |
| 2006/0030039 A1* | 2/2006 | Chen ............................ 435/325 |
| 2006/0060494 A1 | 3/2006 | Goodman et al. |
| 2006/0078993 A1 | 4/2006 | Phan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 7/2006 | Seyda et al. |
| 2006/0188983 A1 | 8/2006 | Harris et al. |
| 2006/0222634 A1 | 10/2006 | Clarke et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragaw et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0092497 A1 | 4/2007 | Hariri |
| 2007/0134210 A1 | 6/2007 | Heidaran |
| 2007/0190034 A1 | 8/2007 | Paludan et al. |
| 2007/0190042 A1 | 8/2007 | Edinger et al. |
| 2007/0275362 A1 | 11/2007 | Edinger et al. |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044848 A1 | 2/2008 | Heidaran |
| 2008/0069895 A1 | 3/2008 | Liu et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0152624 A1 | 6/2008 | Paludan et al. |
| 2008/0152629 A1 | 6/2008 | Edinger et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213228 A1 | 9/2008 | Edinger et al. |
| 2008/0226595 A1 | 9/2008 | Edinger et al. |
| 2009/0053805 A1 | 2/2009 | Hariri |
| 2009/0104164 A1 | 4/2009 | Zhang et al. |
| 2009/0126482 A1 | 5/2009 | Heidaran et al. |
| 2009/0136471 A1 | 5/2009 | Heidaran et al. |
| 2009/0142831 A1 | 6/2009 | Hariri |
| 2009/0226406 A1 | 9/2009 | Hariri |
| 2009/0252710 A1 | 10/2009 | Zhang et al. |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0120015 A1 | 5/2010 | Hariri |
| 2010/0124569 A1 | 5/2010 | Abbot |
| 2010/0143312 A1 | 6/2010 | Hariri |
| 2010/0172830 A1 | 7/2010 | Heidaran |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0311491 A1 | 12/2011 | Edinger et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |
| 2012/0148553 A1 | 6/2012 | Hariri et al. |
| 2012/0171160 A1 | 7/2012 | Abramson et al. |
| 2012/0171161 A1 | 7/2012 | Abramson et al. |
| 2012/0171180 A1 | 7/2012 | Abramson et al. |
| 2012/0171295 A1 | 7/2012 | Abramson et al. |
| 2012/0230959 A1 | 9/2012 | Abbot et al. |
| 2012/0328583 A1 | 12/2012 | Herzberg et al. |
| 2013/0071362 A1 | 3/2013 | Bhatia et al. |
| 2013/0184821 A1 | 7/2013 | Hariri et al. |
| 2013/0243743 A1 | 9/2013 | Heidaran et al. |
| 2013/0259845 A1 | 10/2013 | Heidaran et al. |

OTHER PUBLICATIONS

Clark et al., 2003, "Placental trophoblast from successful human pregnancies expresses the tolerance signaling molecule, CD200 (OX-2)", Am J Reprod Immunol, 50(3):187-195.

Galvin and Jones "Adult human neural stem cells for cell-replacement therapies in the central nervous system," MJA 177:316-318 (2002).

International Search Report dated Jan. 25, 2013 for International application No. PCT/US2012/054493, filed Sep. 10, 2012.

Kamarck, 1987, "Fluorescence-activated cell sorting of hybrid and transfected cells", Methods Enzymol, 151:150-165.

Pawitan, "Prospect of cell therapy for Parkinson's disease," Anatomy Cell Biol 44:256-264 (2011).

Southard et al., 1990, "Important components of the UW solution", Transplantation, 49(2):251-257.

Sugaya, "Neuroreplacement therapy and stem cell biology under disease conditions," Cell. Molec. Life Sci. 60:1891-1902 (2003).

Written Opinion of International Searching Authority dated Jan. 25, 2013 for International application No. PCT/US2012/054493, filed Sep. 10, 2012.

* cited by examiner

TREATMENT OF AMYOTROPHIC LATERAL SCLEROSIS USING PLACENTAL STEM CELLS

This application claims priority benefit of International Application No. PCT/US2012/054493, filed Sep. 10, 2012, which claims priority to U.S. Provisional Application No. 61/533,103, filed Sep. 9, 2011, the disclosures of which are herein incorporated by reference in their entireties.

1. FIELD

Provided herein are methods of treating individuals having amyotrophic lateral sclerosis (ALS) using isolated placental stem cells, e.g., tissue culture surface-adherent placental stem cells.

2. BACKGROUND

Because mammalian placentas are plentiful and are normally discarded as medical waste, they represent a unique source of medically-useful stem cells. There is a need in the medical field for improved compositions and methods of treating amyotrophic lateral sclerosis. The disease is not curable, and the only Food and Drug Administration (FDA)-approved drug treatment is riluzole (RILUTEK®). Other than supportive care, no other therapies exist. As such, provided herein are placental stem cells, and compositions comprising placental stem cells, useful in the treatment of ALS, and methods of using the same to treat ALS.

3. SUMMARY

In one aspect, provided herein is a method of treating amyotrophic lateral sclerosis (ALS) comprising administering to an individual having ALS a therapeutically effective amount of placental stem cells. In certain embodiments, "therapeutically effective" means an amount effective to reduce or ameliorate one or more symptoms of ALS. Also provided herein is a method of treating an individual having ALS, comprising administering to the individual a therapeutically effective amount of placental stem cells, or culture medium conditioned by placental stem cells, wherein the therapeutically effective amount is an amount effective to reduce or ameliorate one or more symptoms of said ALS, e.g., sufficient to cause a detectable improvement in one or more symptoms of ALS, sufficient to delay the onset or worsening of one or more symptoms of ALS, sufficient to reduce the severity of one or more symptoms of ALS, or sufficient to increase the duration or quality of life following onset of symptoms. In another embodiment, provided herein is a method of treating an individual having ALS who exhibits one or more symptoms of ALS, comprising administering to the individual a therapeutically effective amount of placental stem cells, wherein said therapeutically effective amount is an amount that results in reduction or amelioration of one or more of said symptoms of ALS, e.g., improvement in one or more symptoms of ALS, delay of worsening of one or more symptoms of ALS, reduction of severity of one or more symptoms of ALS, or an increase in duration or quality of life following onset of symptoms; monitoring one or more of said symptoms in said patient; and administering a second dose of placental stem cells when said one or more symptoms begins to worsen. In specific embodiments of the above methods, said one or more symptoms comprise difficulty lifting the front part of the foot; difficulty lifting the toes; weakness in one or both legs; weakness in one or both feet; weakness in one or both ankles; hand weakness; hand clumsiness; slurring of speech; trouble swallowing; muscle cramps; twitching in one or both arms; twitching in one or both shoulders and/or twitching of the tongue. In another specific embodiment, said methods above additionally comprise administering a second therapeutic composition, wherein said second therapeutic composition is riluzole, ceftriaxone, dexpramipexole, creatine+tamoxifen, rasagiline, pioglitazone (e.g., pioglitazone HCl), arimoclomol, pyrimethamine, trantinoin+pioglitazone, or an antisense molecule or interfering RNA directed against an RNA encoding superoxide dismutase. In other specific embodiments, said monitoring comprises monitoring over between 1 and 7 days post-administration; monitoring over between 7 and 28 days post administration; or monitoring comprises monitoring over between 1 and 28 weeks post-administration.

In another specific embodiment, said placental stem cells are $CD10^+$, $CD34^-$, $CD105^+$. In a more specific embodiment, said placental stem cells are additionally $CD200^+$. In another specific embodiment, placental stem cells are $CD10^+$, $CD34^-$, $CD105^+$, $CD45^-$ and $CD90^+$. In another specific embodiment, placental stem cells are $CD10^+$, $CD34^-$, $CD105^+$, $CD200^+$, $CD45^-$ and $CD90^+$. In another specific embodiment, placental stem cells are $CD10^+$, $CD34^-$, $CD105^+$, $CD45^-$, $CD90^+$, $CD80^-$ and $CD86^-$. In another specific embodiment, placental stem cells are $CD10^+$, $CD34^-$, $CD105^+$, $CD200^+$, $CD45^-$, $CD90^+$, and $CD80^-$ and $CD86^-$. In other specific embodiments of the above methods, wherein said placental stem cells express CD200 and do not express HLA-G; or express CD73, CD105, and CD200; or express CD200 and OCT-4; or express CD73 and CD105 and do not express HLA-G. In another specific embodiment of any of the above, said placental stem cells are HLA-A,B,$C^+$.

In certain embodiments, said placental stem cells express higher levels of one or more of that following genes ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, wherein the expression of the one or more genes is higher in placental stem cells or umbilical cord stem cells than in bone marrow-derived stem cells, when the stem cells are grown under equivalent conditions.

In certain embodiments of the above methods, said placental stem cells are isolated.

In certain embodiments of the above methods, said placental stem cells are formulated to be administered locally. In certain other embodiments of the above methods, the placental stem cells are formulated to be administered systemically, intravenously, intraarterially, subcutaneously, or intrathecally. In specific embodiments of any of the above methods, said therapeutically effective amount comprises at least $1 \times 10^7$ placental stem cells per administration; at least $1 \times 10^8$ placental stem cells per administration; at least $2 \times 10^8$ placental stem cells per administration; or at least $1 \times 10^9$ placental stem cells per administration.

Unless otherwise indicated, as used herein, the term "about," when referring to a stated numeric value, indicates a value within plus or minus 10% of the stated numeric value.

As used herein, the term "derived" means isolated from or otherwise purified. For example, placental derived adherent cells are isolated from placenta. The term "derived" encompasses cells that are cultured from cells isolated directly from a tissue, e.g., the placenta, and cells cultured or expanded from primary isolates.

As used herein, "immunolocalization" means the detection of a compound, e.g., a cellular marker, using an immune protein, e.g., an antibody or fragment thereof in, for example, flow cytometry, fluorescence-activated cell sorting, magnetic cell sorting, in situ hybridization, immunohistochemistry, or the like.

As used herein, the term "SH2" refers to an antibody that binds an epitope on the marker CD105. Thus, cells that are referred to as $SH2^+$ are $CD105^+$.

As used herein, the terms "SH3" and "SH4" refer to antibodies that bind epitopes present on the marker CD73. Thus, cells that are referred to as $SH3^+$ and/or $SH4^+$ are $CD73^+$.

As used herein, a stem cell is "isolated" if at least 50%, 60%, 70%, 80%, 90%, 95%, or at least 99% of the other cells with which the stem cell is naturally associated are removed from the stem cell, e.g., during collection and/or culture of the stem cell. A population of "isolated" cells means a population of cells that is substantially separated from other cells of the tissue, e.g., placenta, from which the population of cells is derived. In some embodiments, a population of, e.g., stem cells is "isolated" if at least 50%, 60%, 70%, 80%, 90%, 95%, or at least 99% of the cells with which the population of stem cells are naturally associated are removed from the population of stem cells, e.g., during collection and/or culture of the population of stem cells.

As used herein, the term "placental stem cell" refers to a stem cell or progenitor cell that is derived from, e.g., isolated from, a mammalian placenta, regardless of the number of passages after a primary culture, which adheres to a tissue culture substrate (e.g., tissue culture plastic or a fibronectin-coated tissue culture plate). The term "placental stem cell" as used herein does not, however, refer to a trophoblast, a cytotrophoblast, embryonic germ cell, or embryonic stem cell, as those cells are understood by persons of skill in the art. A cell is considered a "stem cell" if the cell retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like. The terms "placental stem cell" and "placenta-derived stem cell" may be used interchangeably. Unless otherwise noted herein, the term "placental" includes the umbilical cord.

As used herein, a stem cell is "positive" for a particular marker when that marker is detectable. For example, a placental stem cell is positive for, e.g., CD73 when CD73 is detectable on the placental stem cell in an amount detectably greater than background (in comparison to, e.g., an isotype control or an experimental negative control for any given assay). A cell is also positive for a marker when that marker can be used to distinguish the cell from at least one other cell type, or can be used to select or isolate the cell when present or expressed by the cell.

As used herein, "immunomodulation" and "immunomodulatory" mean causing, or having the capacity to cause, a detectable change in an immune response. As used herein, "immunosuppression" and "immunosuppressive" mean causing, or having the capacity to cause, a detectable reduction in an immune response.

4. DETAILED DESCRIPTION

4.1 Methods of Treating Amyotrophic Lateral Sclerosis

In one aspect, provided herein is a method of treating ALS comprising administering to an individual having ALS a therapeutically effective amount of placental stem cells. In certain embodiments, "therapeutically effective" means an amount effective to reduce or ameliorate one or more symptoms of ALS, e.g., one or more of: difficulty lifting the front part of the foot and/or toes (footdrop); weakness in one or both legs, feet or ankles; hand weakness or clumsiness; slurring of speech; trouble swallowing; and/or muscle cramps and twitching in the arms, shoulders and/or tongue, e.g., wherein said one or more symptoms are not accounted for by another disease, disorder or condition. In certain embodiments, "therapeutically effective" means an amount effective to delay the onset or worsening of one or more symptoms of ALS, e.g., one or more of: difficulty lifting the front part of the foot and/or toes (footdrop); weakness in one or both legs, feet or ankles; hand weakness or clumsiness; slurring of speech; trouble swallowing; and/or muscle cramps and twitching in the arms, shoulders and/or tongue, e.g., wherein said one or more symptoms are not accounted for by another disease, disorder or condition. In certain embodiments, said "therapeutically effective" amount is an amount sufficient to cause a detectable improvement in one or more symptoms of ALS, sufficient to delay the onset or worsening of one or more symptoms of ALS, sufficient to reduce the severity of one or more symptoms of ALS, or sufficient to increase the duration or quality of life following onset of symptoms. In one embodiment, one or more treatments with placental stem cells results in extension of a treated individual's lifespan by about 1 month, 2 months, 3 months, 4 months, 5 months, 6 months, 7 months, 8 months, 9 months, 10 months, 11 months, 1 year, 13 months, 14 months, 15 months, 16 months, 18 months, 20 months, 2 years, 3 years or more (compared, e.g., to the individual's predicted lifespan in the absence of the placental stem cell treatment). In certain embodiments, a "therapeutically effective" dose of placental stem cells is a dose that results in an appreciable improvement in the individual's speech. In certain embodiments, a "therapeutically effective" dose of placental stem cells is a dose that results in stabilization of the individual's condition, e.g., pulmonary condition, e.g., resulting in removal from a ventilator, reduced time on a ventilator, or delay or elimination in the need for a ventilator.

Administration of placental stem cells can take place once, or more than once. In certain embodiments, placental stem cells are administered multiple times to an individual having ALS, e.g., for as long as symptoms of ALS in the individual persist. In certain embodiments, placental stem cells are administered to an individual having ALS once, twice, or 3, 4, 5, 6, 7, 8, 9, 10, 15, 20, 25, 30, 35, 40, 50, 60, 70, 80, 90, 100 or more times, e.g., for as long as symptoms of ALS in the individual persist. In certain embodiments, placental stem cells are administered to an individual having ALS once per day, e.g., for as long as symptoms of ALS in the individual persist. In certain embodiments, placental stem cells are administered to an individual having ALS once per week, e.g., for as long as symptoms of ALS in the individual persist. In certain embodiments, placental stem cells are administered to an individual having ALS once per month, e.g., for as long as symptoms of ALS in the individual persist. In certain other embodiments, placental stem cells are administered to an individual having ALS twice, three times, four times or more per month. In certain embodiments, placental stem cells are administered to an individual having ALS multiple times over the course of a month, 2 months, 3 months, 4 months, 5 months, 6 months, 7 months, 8 months, 9 months, 10 months, 11 months, 1 year, 2 years, 3 years, 4 years, 5 years, or more. In certain embodiments, an administration of placental stem cells is followed by a period of less than 1 day, or 1 day, 2, days, 3 days, 4 days, 5 days, 6 days, 7 days, 1 week, 2 weeks, 3 weeks, 4 weeks, 1 month, 5 weeks, 6 weeks, 7 weeks, 8 weeks, 2 months, 3 months, or more in which stem cells are not administered before a subsequent administration. In particular embodiments, administration of placental stems cells is according to a cycle in which one, two, three or more administrations is followed by one period of time (e.g., less than 1 day, or 1 day, 2 days, 3 days, 4 days, 5 days, 6 days, 7 days, 1 week, 8 days, 9 days, 10 days, 11 days, 12 days, 13 days, 14 days, 2 weeks, 3 weeks, 4 weeks, 1 month, 5 weeks, 6 weeks, 7, weeks, 8 weeks, 2 months, 3 months or more) which is followed by one, two, three or more administrations, followed by a second period of time (e.g., less than 1 day, or 1 day, 2 days, 3 days, 4 days, 5 days, 6 days, 7 days, 1 week, 8 days, 9 days, 10 days, 11 days, 12 days, 13 days, 14 days, 2 weeks, 3 weeks, 4 weeks, 1 month, 5 weeks, 6 weeks, 7, weeks, 8 weeks, 2 months, 3 months or more) of lesser, equal, or greater duration. Administration of placental stem cells can also take place, e.g., whenever one or more of said symptoms worsens. For example, in certain embodiments, the method comprises identifying an individual patient with ALS who exhibits one or more symptoms of ALS; administering to the individual a therapeutically effective amount of placental stem cells, wherein said therapeutically effective amount is an amount that results in improvement in one or more of said symptoms of ALS; monitoring one or more of said symptoms in said patient; and administering a second dose of placental stem cells when said one or more symptoms begin to worsen. Optionally, this method comprising monitoring and readministration of placental stem cells is repeated 1, 2, 3, 4, 5, 6, 7, 8, 9, 10 or more times during the course of ALS in said individual. In specific embodiments, said individual, or said one or more symptoms, can be monitored for, e.g., 1, 2, 3, 4, 5, 6 or 7 days post-administration, for 1, 2, 3, 4, 5, 6, 7, 8, 9, 10, 11, 12, 13, 14, 15, 16, 17, 18, 19, 20, 21, 22, 23, 24, 25, 26, 27 or 28 weeks after administration, or for 3, 4, 5, 6, 7, 8, 9, 10, 11, 12, 13, 14, 15, 16, 17, 18, 19, 20 or more years after administration, or each separate administration.

In certain embodiments, placental stem cells are administered to an individual in an amount of $1\times10^5$, $3\times10^5$, $5\times10^5$, $1\times10^6$, $3\times10^6$, $5\times10^6$, $1\times10^7$, $3\times10^7$, $5\times10^7$, $1\times10^8$, $2\times10^8$, $3\times10^8$, $4\times10^8$, $5\times10^8$, $6\times10^8$, $7\times10^8$, $8\times10^8$, $8\times10^8$, $1\times10^9$, $2\times10^9$, $3\times10^9$, $4\times10^9$, $5\times10^9$, $1\times10^{10}$, $5\times10^{10}$, or $1\times10^{11}$ or more placental stem cells per administration. In certain embodiments, placental stem cells are administered to an individual in an amount of $1\times10^5$–$5\times10^5$, $5\times10^5$–$1\times10^6$, $1\times10^6$–$5\times10^6$, $5\times10^6$–$1\times10^7$, $1\times10^7$–$5\times10^7$, $5\times10^7$–$1\times10^8$, $1\times10^8$–$5\times10^8$, $5\times10^8$–$1\times10^9$, $1\times10^9$–$5\times10^9$, $5\times10^9$–$1\times10^{10}$, $1\times10^{10}$–$5\times10^{10}$, $5\times10^{10}$–$1\times10^{11}$ or more placental stem cells per administration. In certain embodiments, placental stem cells are administered to an individual in an amount of $1\times10^5$, $3\times10^5$, $5\times10^5$, $1\times10^6$, $3\times10^6$, $5\times10^6$, $1\times10^7$, $3\times10^7$, $5\times10^7$, $1\times10^8$, $2\times10^8$, $3\times10^8$, $4\times10^8$, $5\times10^8$, $6\times10^8$, $7\times10^8$, $8\times10^8$, $8\times10^8$, $1\times10^9$, $2\times10^9$, $3\times10^9$, $4\times10^9$, $5\times10^9$, $1\times10^{10}$, $5\times10^{10}$, or $1\times10^{11}$ or more placental stem cells per day. In certain embodiments, placental stem cells are administered to an individual in an amount of $1\times10^5$–$5\times10^5$, $5\times10^5$–$1\times10^6$, $1\times10^6$–$5\times10^6$, $5\times10^6$–$1\times10^7$, $1\times10^7$–$5\times10^7$, $5\times10^7$–$1\times10^8$, $1\times10^8$–$5\times10^8$, $5\times10^8$–$1\times10^9$, $1\times10^9$–$5\times10^9$, $5\times10^9$–$1\times10^{10}$, $1\times10^{10}$–$5\times10^{10}$, $5\times10^{10}$–$1\times10^{11}$ or more placental stem cells per day.

In certain embodiments, the method of treatment additionally comprises administration to the individual with ALS of one or more doses of a second therapeutic composition. The second therapeutic composition may be administered to the individual having ALS once, or more than once; at the same time as said placental stem cells are administered, or at different times; etc. In certain embodiments, the second therapeutic compound is riluzole, ceftriaxone, dexpramipexole, creatine+tamoxifen, rasagiline, pioglitazone (e.g., pioglitazone HCl), arimoclomol, pyrimethamine, trantinoin+pioglitazone, fluoxetine, duloxetine, cannabinoid agonist or partial agonist, lithium, olexisome, or an antisense molecule or interfering RNA directed against an RNA encoding superoxide dismutase. In one embodiment, the second therapeutic compound is not olexisome.

In certain embodiments, the method of treating ALS comprises monitoring immunosuppression by said placental stem cells in said individual, e.g., following administration of the cells. Such monitoring can be used, e.g., as a surrogate for monitoring symptoms, or as a way of determining when additional dosing is warranted. In certain more specific embodiments, the method additionally comprises correlating said immunosuppression with reduction in one or more of said symptoms of ALS. For example, the method of treatment can comprise: (1) administering to an individual having ALS placental stem cells such that one or more symptoms of said ALS are reduced; and (2) monitoring the individual to determine the level of immunosuppression due to said placental stem cells. Such monitoring can comprise, for example, monitoring the activity of peripheral blood mononuclear cells, e.g., T cells, macrophages and/or dendritic cells from the individual against an antigen in, e.g., a one-way mixed lymphocyte reaction (MLR) assay, post-administration to determine the degree of immunosuppression by the placental stem cells, e.g., over time.

In certain embodiments of the method of treatment, the individual is administered an amount of placental stem cells that results in a suppression of immune cell activity by, e.g., 20%, 30%, 40%, 50%, 60%, 70% or 80%, as compared to an equivalent number of said immune cells' activity before administration of placental stem cells. The individual is monitored for any increase in the activity of the immune cells, e.g., within 1, 2, 3, 4, 5, 6, 7, 8, 9, 10, 11, 12, 13, 14, 15, 16, 17, 18, 19, 20 or 21 days of said administration; if the activity of the immune cells increases to a predetermined level, e.g., 30%, 40%, 50%, 60%, 70%, 80%, of 90% pre-administration activity, placental stem cells are administered again. In certain embodiments, the treatment is administered to a human individual. In certain embodiments, the human individual is a child. In certain embodiments, the human individual is an adolescent. In certain embodiments, the human individual is an adult. In certain embodiments, the human individual is an elderly adult. In certain embodiments, the human individual is aged 40 years or more, 50 years or more, 60 years or more, 70 years or more, 80 years or more, or 90 years or more. In certain embodiments, the treatment is administered to a male individual, for example, a male human individual. In other embodiments, the treatment is administered to a female individual, for example, a female human individual. In certain embodiments, the treatment is administered to an individual with one or more mutations in the Cu/Zn Superoxide Dismutase 1 gene (SOD1). In other embodiments, the treatment is administered to an individual who does not have a mutation in SOD1, or wherein the individual's SOD1 mutations are not known to be associated with ALS. In certain other embodiments, the treatment is administered to an individual who has ALS, wherein the individual has one or more mutations in one or more of the genes ALS2, ANG, APOE, ATXN2, C9orf72, CRYM, DAO, DCTN1, DPP6, ELP3, FIG4, FUS, HFE, KIFAP3, LUM, NEFH, OPTN, PON1, SETX, SIGMAR1, SMN, SPG11, SQSTM1, TAF15, TARDBP (TDP43), UBQLN2, VAPB, VCP, or VEGF. See, e.g., Andersen & Al-Chalabi, 2011, *Nat. Rev. Neurol.* 7: 603-615. In a particular embodiment, the individual has been diagnosed with sporadic ALS. In another embodiment, the individual has been diagnosed with familial ALS.

Placental stem cells used for treatment of ALS can be derived from, e.g., isolated from and/or expanded from, a single species, e.g., the species of the intended recipient or the species of the immune cells the function of which is to be reduced or suppressed, or can be derived from multiple species. In certain embodiments, the placental stem cells can be derived from one or more individuals of the same species as the intended recipient. In certain embodiments, the placental stem cells can be derived from one or more individuals of the same sex as the intended recipient. In certain embodiments, the placental stem cells are maternal in origin and are derived from the same individual for whom the treatment is intended. In certain embodiments, the placental stem cells are fetal in origin and are derived from the fetus of the same individual for whom the treatment is intended. In certain embodiments, the placental stem cells are both maternal and fetal in origin and comprise cells derived from the same individual for whom the treatment is intended. In certain other embodiments, the placental stem cells are obtained from a placental stem cell bank or other type of cell bank.

4.2 Monitoring of Immunomodulation by Placental Stem Cells

In certain embodiments, placental stem cells can be used to reduce activation of immune cells associated with ALS, e.g., to reduce an immune response associated with, or causative of, ALS. An "immune cell" in the context of this method means any cell of the immune system, particularly T cells and NK (natural killer) cells. Thus, in various embodiments of the method, placental stem cells are contacted with a plurality of immune cells, wherein the plurality of immune cells are, or comprises, a plurality of T cells (e.g., a plurality of $CD3^+$ T cells, $CD4^+$ T cells and/or $CD8^+$ T cells) and/or natural killer cells. In certain embodiments of the method, placental stem cells are brought into proximity with a plurality of immune cells, wherein the plurality of immune cells are, or comprises, a plurality of T cells (e.g., a plurality of $CD3^+$ T cells, $CD4^+$ T cells and/or $CD8^+$ T cells) and/or natural killer cells, wherein the proximity is sufficient to reduce activation of immune cells associated with ALS, e.g., to reduce an immune response associated with, or causative of, ALS. Hereinafter, unless noted otherwise, the term "proximity" refers to sufficient proximity to elicit the desired result. An "immune response" in the context of the method can be any response by an immune cell to a stimulus normally perceived by an immune cell, e.g., a response to the presence of an antigen. In various embodiments, an immune response can be the proliferation of T cells (e.g., $CD3^+$ T cells, $CD4^+$ T cells and/or $CD8^+$ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, or the like.

Placental stem cells can be tested, e.g., prior to administration to an individual having ALS, e.g., in an MLR comprising combining $CD4^+$ or $CD8^+$ T cells, dendritic cells (DC) and placental stem cells in a ratio of about 10:1:2, wherein the T cells are stained with a dye such as, e.g., CFSE that partitions into daughter cells, and wherein the T cells are allowed to proliferate for about 6 days. The T cells and/or DC cells can be obtained from the individual to be treated, e.g., can be autologous to the individual, or can be allogeneic to the individual. The placental stem cells are immunosuppressive if the T cell proliferation at 6 days in the presence of placental stem cells is detectably reduced compared to T cell proliferation in the presence of DC and absence of placental stem cells. In one embodiment of an MLR, for example, placental stem cells can be either thawed or harvested from culture. About 20,000 placental stem cells are resuspended in 100 µl of medium (RPMI 1640, 1 mM HEPES buffer, antibiotics, and 5% pooled human serum), and allowed to attach to the bottom of a well for 2 hours. $CD4^+$ and/or $CD8^+$ T cells are isolated from whole peripheral blood mononuclear cells using Miltenyi magnetic beads. The cells are CFSE stained, and a total of 100,000 T cells ($CD4^+$ T cells alone, $CD8^+$ T cells alone, or equal amounts of $CD4^+$ and $CD8^+$ T cells) are added per well. The volume in the well is brought to 200 µl, and the MLR is allowed to proceed.

In certain embodiments, the anti-inflammatory activity (i.e., immunosuppressive activity) of the placental stem cells is determined prior to administration to the individual having ALS. This can be accomplished, for example, by determining the immunosuppressive activity of a sample of the placental stem cells to be administered for treatment of ALS. Such an activity can be determined, for example, by testing a sample of the placental stem cells or placental stem cells in, e.g., an MLR or regression assay. In one embodiment, an MLR is performed with the sample, and a degree of immunosuppression demonstrated by the sample placental stem cells in the assay is determined. In certain embodiments, the degree of reduction of a symptom of ALS is expected to correlate with the immunosuppressive activity of the sampled placental stem cells.

The parameters of the MLR can be varied to provide more data or to best determine the capacity of a sample of a population of placental stem cells to immunosuppress. For example, because immunosuppression by placental stem cells appears to increase in proportion to the number of placental stem cells present in the assay, the MLR can be performed with, in one embodiment, two or more numbers of placental stem cells, e.g., $1\times10^3$, $3\times10^3$, $1\times10^4$ and/or $3\times10^4$ placental stem cells per reaction. The number of placental stem cells relative to the number of T cells in the assay can also be varied. For example, placental stem cells and T cells in the assay can be present in any ratio of, e.g. about 10:1 to about 1:10, preferably about 1:5, though a relatively greater number of placental stem cells or T cells can be used.

The regression assay or BTR assay can be used in similar fashion.

Placental stem cells can be administered to an individual in a ratio, with respect to a known or expected number of immune cells, e.g., T cells, in the individual, of from about 10:1 to about 1:10, preferably in some embodiments about 1:5. However, placental stem cells can be administered to an individual in a ratio of, in non-limiting examples, about 10,000:1, about 1,000:1, about 100:1, about 10:1, about 1:1, about 1:10, about 1:100, about 1:1,000 or about 1:10,000. In certain embodiments, about $1\times10^5$ to about $1\times10^8$ placental stem cells per recipient kilogram, preferably about $1\times10^6$ to about $1\times10^7$ placental stem per recipient kilogram can be administered to effect immunosuppression. In various embodiments, placental stem cells administered to an individual or subject comprise at least, about, or no more than, $1\times10^5$, $3\times10^5$, $5\times10^5$, $1\times10^6$, $3\times10^6$, $5\times10^6$, $1\times10^7$, $3\times10^7$, $5\times10^7$, $1\times10^8$, $2\times10^8$, $3\times10^8$, $4\times10^8$, $5\times10^8$, $6\times10^8$, $7\times10^8$, $8\times10^8$, $8\times10^8$, $1\times10^9$, $2\times10^9$, $3\times10^9$, $4\times10^9$, $5\times10^9$, $1\times10^{10}$, $5\times10^{10}$, or $1\times10^{11}$ or more placental stem cells. In various embodiments, placental stem cells administered to an individual or subject comprise at least, about, or no more than, $1\times10^5$–$5\times10^5$, $5\times10^5$–$1\times10^6$, $1\times10^6$–$5\times10^6$, $5\times10^6$–$1\times10^7$, $1\times10^7$–$5\times10^7$, $5\times10^7$–$1\times10^8$, $1\times10^8$–$5\times10^8$ $1\times10^9$–$5\times10^9$, $5\times10^9$–$1\times10^{10}$, $1\times10^{10}$–$5\times10^{10}$, $5\times10^{10}$–$1\times10^{11}$ or more placental stem cells.

The placental stem cells can also be administered with one or more second types of stem cells, e.g., mesenchymal stem cells from bone marrow, neural stem cells from brain or spinal cord, or stem cells from fat tissue. Such second stem cells can be administered to an individual with said placental stem cells in a ratio of, e.g., between about 1:10 to about 10:1.

To facilitate contacting, or proximity, of placental stem cells and immune cells in vivo, the placental stem cells can be administered to an individual by any route sufficient to bring the placental stem cells and immune cells into contact with or proximity to each other. For example, the placental stem cells can be administered to the individual, e.g., intravenously, intramuscularly, intraperitoneally, intraocularly, parenterally, intrathecally, intraarterially, subcutaneously, or directly into an organ, e.g., pancreas. The placental stem cells can be formulated as a pharmaceutical composition as described in 4.7.1.2, below.

In another aspect, the placental stem cells administered to the individual having ALS have been genetically engineered to express one or more anti-inflammatory cytokines. In a specific embodiment, said anti-inflammatory cytokine is IL-10.

4.3 Placental Stem Cells and Placental Stem Cell Populations

The methods of treating an individual having ALS provided herein comprise administering tissue culture surface-adherent placental stem cells, e.g., tissue culture plastic-adherent placental stem cells to the individual, e.g., a therapeutically effective amount of said placental stem cells. In certain embodiments, the placental stem cells also have, in sufficient numbers, the capacity to detectably suppress an immune function, e.g., proliferation of CD4$^+$ and/or CD8$^+$ T cells in a mixed lymphocyte reaction assay or regression assay.

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristics discussed below.

The placental stem cells disclosed herein are, in certain embodiments, multipotent in vitro (that is, the cells differentiate in vitro under differentiating conditions), multipotent in vivo (that is, the cells differentiate in vivo), or both. In certain embodiments, the placental stem cells disclosed herein do not engraft in vivo.

4.3.1 Physical and Morphological Characteristics

The placental stem cells used as described herein, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cytoplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also distinguishable from hematopoietic stem cells, which generally assume a more rounded, or cobblestone, morphology in culture.

4.3.2 Cell Surface, Molecular and Genetic Markers

The isolated placental stem cells, e.g., isolated multipotent placental stem cells, and populations of such isolated placental stem cells, useful in the methods disclosed herein, e.g., the methods of treatment of ALS, are tissue culture surface-adherent human placental stem cells that have characteristics of multipotent cells or stem cells, and express a plurality of markers that can be used to identify and/or isolate the cells, or populations of cells that comprise the stem cells. The isolated placental stem cells, and placental cell populations (e.g., two or more isolated placental stem cells) described herein include placental stem cells and placental cell-containing cell populations obtained directly from the placenta, or any part thereof (e.g., chorion, placental cotyledons, or the like), or that are cultured from such cells. Isolated placental cell populations also include populations of (that is, two or more) isolated placental stem cells in culture, and a population in a container, e.g., a bag. The isolated placental stem cells described herein are not bone marrow-derived mesenchymal cells, adipose-derived mesenchymal stem cells, or mesenchymal cells obtained from umbilical cord blood, placental blood, or peripheral blood. Placental cells, e.g., placental multipotent cells and placental stem cells, useful in the methods and compositions described herein are described herein and, e.g., in U.S. Pat. Nos. 7,311,904; 7,311,905; 7,468,276; and 8,057,788, the disclosures of which are hereby incorporated by reference in their entireties.

In certain embodiments, the isolated placental stem cells are CD34$^-$, CD10$^+$ and CD105$^+$ as detectable by flow cytometry. In another specific embodiment, the isolated CD34$^-$, CD10$^+$, CD105$^+$ placental stem cells have the potential to differentiate into cells of a neural phenotype, cells of an osteogenic phenotype, and/or cells of a chondrogenic phenotype. In another specific embodiment, the isolated CD34$^-$, CD10$^+$, CD105$^+$ placental stem cells are additionally CD200$^+$ as detectable by flow cytometry. In another specific embodiment, the isolated CD34$^-$, CD10$^+$, CD105$^+$ placental stem cells are additionally CD45$^-$ or CD90$^+$ as detectable by flow cytometry. In another specific embodiment, the isolated CD34$^-$, CD10$^+$, CD105$^+$ placental stem cells are additionally CD45$^-$ and CD90$^+$ as detectable by flow cytometry. In another specific embodiment, the isolated CD34$^-$, CD10$^+$, CD105$^+$, CD200$^+$ placental stem cells are additionally CD90$^+$ or CD45$^-$ as detectable by flow cytometry. In another specific embodiment, the isolated CD34$^-$, CD10$^+$, CD105$^+$, CD200$^+$ placental stem cells are additionally CD90$^+$ and CD45$^-$ as detectable by flow cytometry, i.e., the cells are CD34$^-$, CD10$^+$, CD45$^-$, CD90$^+$, CD105$^+$ and CD200$^+$. In another specific embodiment, said CD34$^-$, CD10$^+$, CD45$^-$, CD90$^+$, CD105$^+$ CD200$^+$ placental stem cells are additionally CD80⁻ and CD86⁻ as detectable by flow cytometry. In certain specific embodiments of any of the embodiments herein, the placental stem cells are additionally OCT-4⁺ as detectable by, e.g., reverse-transcriptase polymerase chain reaction (RT-PCR).

Isolated placental stem cells generally do not express alpha smooth muscle actin (αSMA), e.g., as detectable by immunolocalization. Isolated placental stem cells generally express MHC Class I molecules, e.g., HLA-A,B,C as detectable by flow cytometry.

In certain embodiments, said placental stem cells are CD34⁻, CD10⁺, CD105⁺ and CD200⁺ and one or more of CD38⁻, CD45⁻, CD80⁻, CD86⁻, CD133⁻, HLA-DR,DP, DQ⁻, SSEA3⁻, SSEA4⁻, CD29⁺, CD44⁺, CD73⁺, CD90⁺, CD105⁺, HLA-A,B,C⁺, PDL1⁺, ABC-p⁺, and/or OCT-4⁺ as detectable by flow cytometry. In other embodiments, any of the CD34⁻, CD10⁺, CD105⁺ placental stem cells described above are additionally one or more of CD29⁺, CD38⁻, CD44⁺, CD54⁺, SH3⁺ or SH4⁺ as detectable by flow cytometry. In another specific embodiment, the placental stem cells are additionally CD44⁺ as detectable by flow cytometry. In another specific embodiment of any of the isolated CD34⁻, CD10⁺, CD105⁺ placental stem cells above, the cells are additionally one or more of CD117⁻, CD133⁻, KDR⁻ (VEGFR2⁻), HLA-A,B,C⁺, HLA-DP,DQ,DR⁻, or Programmed Death-1 Ligand (PDL1)⁺, or any combination thereof, as detectable by flow cytometry.

In another embodiment, the CD34⁻, CD10⁺, CD105⁺ placental stem cells are additionally one or more of CD13⁺, CD29⁺, CD33⁺, CD38⁻, CD44⁺, CD45⁻, CD54⁺, CD62E⁻, CD62L⁻, CD62P⁻, SH3⁺ (CD73⁺), SH4⁺ (CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR (VEGFR2), HLA-A,B,C⁺, HLA-DP,DQ,DR⁻, HLA-G⁻, or Programmed Death-1 Ligand (PDL1)⁺, or any combination thereof, as detectable by flow cytometry. In another embodiment, the CD34⁻, CD10⁺, CD105⁺ placental stem cells are additionally CD13⁺, CD29⁺, CD33⁺, CD38⁻, CD44⁺, CD45⁻, CD54/ICAM⁺, CD62E⁻, CD62L⁻, CD62P⁻, SH3⁺ (CD73⁺), SH4⁺ (CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR (VEGFR2⁻), HLA-A,B,C⁺, HLA-DP,DQ,DR⁻, HLA-G⁻, and Programmed Death-1 Ligand (PDL1)⁺ as detectable by flow cytometry.

In another specific embodiment, any of the placental stem cells described herein are additionally ABC-p⁺, as detectable by flow cytometry, or OCT-4⁺ (POU5F1⁺), as detectable by RT-PCR, wherein ABC-p is a placenta-specific ABC transporter protein (also known as breast cancer resistance protein (BCRP) or as mitoxantrone resistance protein (MXR)), and OCT-4 is the Octamer-4 protein (POU5F1). In another specific embodiment, any of the placental stem cells described herein are additionally SSEA3⁻ or SSEA4⁻, as detectable by flow cytometry, wherein SSEA3 is Stage Specific Embryonic Antigen 3, and SSEA4 is Stage Specific Embryonic Antigen 4. In another specific embodiment, any of the placental stem cells described herein are additionally SSEA3⁻ and SSEA4⁻.

In another specific embodiment, any of the placental stem cells described herein are, or are additionally, one or more of MHC-I⁺ (e.g., HLA-A,B,C⁺), MHC-II⁻ (e.g., HLA-DP,DQ, DR⁻) or HLA-G⁻ as detectable by flow cytometry. In another specific embodiment, any of the placental stem cells described herein are additionally MHC-I⁺ (e.g., HLA-A,B, C⁺), MHC-II⁻ (e.g., HLA-DP,DQ,DR⁻) and HLA-G⁻ as detectable by flow cytometry.

Also provided herein are populations of the isolated placental stem cells, or populations of cells, e.g., populations of placental cells, comprising, e.g., that are enriched for, the isolated placental stem cells, that are useful in the methods and compositions disclosed herein. Preferred populations of cells are those comprising the isolated placental stem cells, wherein the populations of cells comprise, e.g., at least 10%, 15%, 20%, 25%, 30%, 35%, 40%, 45%, 50%, 55%, 60%, 65%, 70%, 75%, 80%, 85%, 90%, 95% or 98% isolated CD10⁺, CD105⁺ and CD34⁻ placental stem cells, as detectable by flow cytometry; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated CD10⁺, CD105⁺ and CD34⁻ placental stem cells as detectable by flow cytometry. In a specific embodiment, the isolated CD34⁻, CD10⁺, CD105⁺ placental stem cells are additionally CD200⁺ as detectable by flow cytometry. In another specific embodiment, the isolated CD34⁻, CD10⁺, CD105⁺, CD200⁺ placental stem cells are additionally CD90⁺ or CD45⁻ as detectable by flow cytometry. In another specific embodiment, the isolated CD34⁻, CD10⁺, CD105⁺, CD200⁺ placental stem cells are additionally CD90⁺ and CD45⁻ as detectable by flow cytometry. In another specific embodiment, any of the isolated CD34⁻, CD10⁺, CD105⁺ placental stem cells described above are additionally one or more of CD29⁺, CD38⁻, CD44⁺, CD54⁺, SH3⁺ or SH4⁺ as detectable by flow cytometry. In another specific embodiment, the isolated CD34⁻, CD10⁺, CD105⁺ placental stem cells, or isolated CD34⁻, CD10⁺, CD105⁺, CD200⁺ placental stem cells, are additionally CD44⁺ as detectable by flow cytometry. In a specific embodiment of any of the populations of cells comprising isolated CD34⁻, CD10⁺ CD105⁺ placental stem cells above, the isolated placental stem cells are additionally one or more of CD13⁺, CD29⁺, CD33⁺, CD38⁻, CD44⁺, CD45⁻, CD54⁺, CD62E⁻, CD62L⁻, CD62E⁻, SH3⁺ (CD73⁺), SH4⁺ (CD73⁺), CD80⁻, CD86⁻, CD90⁺ SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁻, or Programmed Death-1 Ligand (PDL1)⁺, or any combination thereof, as detectable by flow cytometry. In another specific embodiment, the CD34⁻, CD10⁺, CD105⁺ placental stem cells are additionally CD13⁺, CD29⁺, CD33⁺, CD38⁻, CD44⁺, CD45⁻, CD54/ICAM⁺, CD62E⁻, CD62L⁻, CD62E⁻, SH3⁺ (CD73⁺), SH4⁺ (CD73⁺), CD80⁻, CD86⁻, CD90⁺ SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁻, and Programmed Death-1 Ligand (PDL1)⁺ as detectable by flow cytometry.

In certain embodiments, the isolated placental stem cells in said population of cells are one or more, or all, of CD10⁺, CD29⁺, CD34⁻, CD38⁻, CD44⁺, CD45⁻, CD54⁺, CD90⁺ SH2⁺, SH3⁺ SH4⁺, SSEA3⁻, SSEA4⁻, OCT-4⁺, and ABC-p⁺ as detectable by flow cytometry, wherein said isolated placental stem cells are obtained, or are obtainable, by physical and/or enzymatic disruption of placental tissue. In a specific embodiment, the isolated placental stem cells are OCT-4⁺ as detectable by RT-PCR and ABC-p⁺ as detectable by flow cytometry. In another specific embodiment, the isolated placental stem cells are OCT-4⁺ and CD34⁻, wherein said isolated placental stem cells have at least one of the following characteristics: CD10⁺, CD29⁺, CD44⁺, CD45⁻, CD54⁺, CD90⁺ SH3⁺, SH4⁺ SSEA3⁻, and SSEA4⁻ as detectable by flow cytometry. In another specific embodiment, the isolated placental stem cells are OCT-4$^+$, CD34$^-$, CD10$^+$, CD29$^+$, CD44$^+$, CD45$^-$, CD54$^+$, CD90$^+$ SH3$^+$, SH4$^+$ SSEA3$^-$, and SSEA4$^-$ as detectable by flow cytometry. In another embodiment, the isolated placental stem cells are OCT-4$^+$, CD34$^-$, SSEA3$^-$, and SSEA4$^-$ as detectable by flow cytometry. In another specific embodiment, the isolated placental stem cells are OCT-4$^+$ and CD34$^-$, and are either SH2$^+$ or SH3$^+$ as detectable by flow cytometry. In another specific embodiment, the isolated placental stem cells are OCT-4$^+$, CD34$^-$, SH2$^+$ and SH3$^+$ as detectable by flow cytometry. In another specific embodiment, the isolated placental stem cells are OCT-4$^+$, CD34$^-$, SSEA3$^-$, and SSEA4$^-$, and are either SH2$^+$ or SH3$^+$ as detectable by flow cytometry. In another specific embodiment, the isolated placental stem cells are OCT-4$^+$ and CD34$^-$, and either SH2$^+$ or SH3$^+$, and are at least one of CD10$^+$, CD29$^+$, CD44$^+$, CD45$^-$, CD54$^+$, CD90$^+$ SSEA3$^-$, or SSEA4$^-$ as detectable by flow cytometry. In another specific embodiment, the isolated placental stem cells are OCT-4$^+$, CD34$^-$, CD10$^+$, CD29$^+$, CD44$^+$, CD45$^-$, CD54$^+$, CD90$^+$ SSEA3$^-$, and SSEA4$^-$, and are either SH2$^+$ or SH3$^+$ as detectable by flow cytometry.

In another embodiment, the isolated placental stem cells are SH2$^+$, SH3$^+$ SH4$^+$ as detectable by flow cytometry, and OCT-4$^+$ as detectable by RT-PCR. In another specific embodiment, the isolated placental stem cells are CD10$^+$, CD29$^+$, CD44$^+$, CD54$^+$, CD90$^+$, CD34$^-$, CD45$^-$, SSEA3$^-$, or SSEA4$^-$ as detectable by flow cytometry. In another embodiment, the isolated placental stem cells are SH2$^+$, SH3$^+$ SH4$^+$, SSEA3$^-$ and SSEA4$^-$ as detectable by flow cytometry. In another specific embodiment, the isolated placental stem cells are SH2$^+$, SH3$^+$ SH4$^+$, SSEA3$^-$ and SSEA4$^-$, and CD10$^+$, CD29$^+$, CD44$^+$, CD54$^+$, CD90$^+$, OCT-4$^+$, CD34$^-$ or CD45$^-$ as detectable by flow cytometry. In another specific embodiment, the isolated placental stem cells are SH2$^+$ SH3$^+$, SH4$^+$, SSEA3$^-$, SSEA4$^-$, CD10$^+$, CD29$^+$, CD44$^+$, CD54$^+$, CD90$^+$, OCT-4$^+$, CD34$^-$ and CD45$^-$ as detectable by flow cytometry.

In another embodiment, the isolated placental stem cells useful in the methods and compositions disclosed herein are CD10$^+$, CD29$^+$, CD34$^-$, CD44$^+$, CD45$^-$, CD54$^+$, CD90$^+$, SH2$^+$, SH3$^+$ and SH4$^+$ as detectable by flow cytometry; wherein said isolated placental stem cells are additionally one or more of OCT-4$^+$ as detectable by RT-PCR, or SSEA3$^-$ or SSEA4$^-$ as detectable by flow cytometry.

In certain embodiments, isolated placental stem cells are CD200$^+$ or HLA-G$^-$ as detectable by flow cytometry. In a specific embodiment, the isolated placental stem cells are CD200$^+$ and HLA-G$^-$ as detectable by flow cytometry. In another specific embodiment, the isolated placental stem cells are additionally CD73$^+$ and CD105$^+$ as detectable by flow cytometry. In another specific embodiment, the isolated placental stem cells are additionally CD34$^-$, CD38$^-$ or CD45$^-$ as detectable by flow cytometry. In another specific embodiment, the isolated placental stem cells are additionally CD34$^-$, CD38$^-$ and CD45$^-$ as detectable by flow cytometry. In another specific embodiment, said placental stem cells are CD34$^-$, CD38$^-$, CD45$^-$, CD73$^+$ and CD105$^+$ as detectable by flow cytometry. In another specific embodiment, the isolated placental stem cells are isolated away from placental cells that are not said placental stem cells.

In another embodiment, a cell population useful in the methods described herein is a population of cells comprising, e.g., that is enriched for, CD200$^+$, HLA-G$^-$ placental stem cells, e.g., as detectable by flow cytometry. In a specific embodiment, said population is a population of placental cells. In certain embodiments, at least about 10%, at least about 20%, at least about 30%, at least about 40%, at least about 50%, at least about 60%, at least about 70%, at least about 80%, at least about 90%, at least about 95%, or at least about 99% of cells in said cell population are isolated CD200$^+$, HLA-G$^-$ placental stem cells, e.g., as detectable by flow cytometry. In various embodiments, at least about 10%, at least about 20%, at least about 30%, at least about 40%, at least about 50%, or at least about 60%, of cells in said cell population are isolated CD200$^+$ HLA-G$^-$ placental stem cells, e.g., as detectable by flow cytometry. In one embodiment, at least about 70% of cells in said cell population are isolated CD200$^+$, HLA-G$^-$ placental stem cells, e.g., as detectable by flow cytometry. In one embodiment, at least about 80%, 90%, 95%, or 99% of said cells are isolated CD200$^+$, HLA-G$^-$ placental stem cells, e.g., as detectable by flow cytometry. In a specific embodiment of the cell populations, said isolated CD200$^+$, HLA-G$^-$ placental stem cells are also CD73$^+$ and CD105$^+$, e.g., as detectable by flow cytometry. In another specific embodiment, said isolated CD200$^+$, HLA-G$^-$ placental stem cells are also CD34$^-$, CD38$^-$ or CD45$^-$, e.g., as detectable by flow cytometry. In another specific embodiment, said isolated CD200$^+$, HLA-G$^-$ placental stem cells are also CD34$^-$, CD38$^-$, CD45$^-$, CD73$^+$ and CD105$^+$, e.g., as detectable by flow cytometry. In another specific embodiment, said cell population is isolated away from placental cells that are not placental stem cells. In another specific embodiment, said isolated CD200$^+$, HLA-G$^-$ placental stem cells are isolated away from placental cells that do not display these markers.

In another embodiment, the isolated placental stem cells useful in the methods and compositions described herein are CD73$^+$, CD105$^+$, and CD200$^+$, e.g., as detectable by flow cytometry. In another specific embodiment, the isolated placental stem cells are HLA-G$^-$, e.g., as detectable by flow cytometry. In another specific embodiment, the isolated placental stem cells are CD34$^-$, CD38$^-$ or CD45$^-$, e.g., as detectable by flow cytometry. In another specific embodiment, the isolated placental stem cells are CD34$^-$, CD38$^-$ and CD45$^-$, e.g., as detectable by flow cytometry. In another specific embodiment, the isolated placental stem cells are CD34$^-$, CD38$^-$, CD45$^-$, and HLA-G$^-$, e.g., as detectable by flow cytometry. In another specific embodiment, the isolated placental stem cells are isolated away from placental cells that are not the isolated placental stem cells. In another specific embodiment, the isolated placental stem cells are isolated away from placental cells that do not display these markers.

In another embodiment, a cell population useful in the methods and compositions described herein is a population of cells comprising, e.g., that is enriched for, isolated CD73$^+$ CD105$^+$, CD200$^+$ placental stem cells, e.g., as detectable by flow cytometry. In certain embodiments, at least about 10%, at least about 20%, at least about 30%, at least about 40%, at least about 50%, or at least about 60% of cells, at least about 70%, at least about 80%, at least about 90%, at least about 95%, or at least about 99% of cells in said cell population are isolated CD73$^+$, CD105$^+$, CD200$^+$ placental stem cells, e.g., as detectable by flow cytometry. In various embodiments, at least about 10%, at least about 20%, at least about 30%, at least about 40%, at least about 50%, or at least about 60% of cells in said cell population are isolated CD73$^+$ CD105$^+$, CD200$^+$ placental stem cells, e.g., as detectable by flow cytometry. In another embodiment, at least about 70% of said cells in said population of cells are isolated CD73$^+$, CD105$^+$, CD200$^+$ placental stem cells, e.g., as detectable by flow cytometry. In another embodiment, at least about 80%, 90%, 95%, or 99% of cells in said population of cells are isolated CD73$^+$, CD105$^+$, CD200$^+$ placental stem cells, e.g., as detectable by flow cytometry. In a specific embodiment of said populations, the isolated placental stem cells are HLA-G$^-$, e.g., as detectable by flow cytometry. In another specific embodiment, the isolated placental stem cells are additionally CD34$^-$, CD38$^-$ or CD45$^-$, e.g., as detectable by flow cytometry. In another specific embodiment, the isolated placental stem cells are additionally CD34$^-$, CD38$^-$ and CD45$^-$, e.g., as detectable by flow cytometry. In another specific embodiment, the isolated placental stem cells are additionally CD34$^-$, CD38$^-$, CD45$^-$, and HLA-G$^-$, e.g., as detectable by flow cytometry. In another specific embodiment, said population of placental stem cells is isolated away from placental cells that are not placental stem cells. In another specific embodiment, said population of placental stem cells is isolated away from placental cells that do not display these characteristics.

In certain other embodiments, the isolated placental stem cells are one or more of CD10$^+$, CD29$^+$, CD34$^-$, CD38$^-$, CD44$^+$, CD45$^-$, CD54$^+$, CD90$^+$ SH2$^+$, SH3$^+$ SH4$^+$, SSEA3$^-$, SSEA4$^-$, HLA-G$^-$ or ABC-p$^+$, e.g., as detectable by flow cytometry, or OCT-4$^+$, as detectable by RT-PCR. In a specific embodiment, the isolated placental stem cells are CD10$^+$, CD29$^+$, CD34$^-$, CD38$^-$, CD44$^+$, CD45$^-$, CD54$^+$, CD90$^+$ SH2$^+$, SH3$^+$ SH4$^+$, SSEA3$^-$, SSEA4$^-$, and OCT-4$^+$, e.g., as detectable by flow cytometry. In another specific embodiment, the isolated placental stem cells are CD10$^+$, CD29$^+$, CD34$^-$, CD38$^-$, CD45$^-$, CD54$^+$ SH2$^+$, SH3$^+$ and SH4$^+$, e.g., as detectable by flow cytometry. In another specific embodiment, the isolated placental stem cells are CD10$^+$, CD29$^+$, CD34$^-$, CD38$^-$, CD45$^-$, CD54$^+$, SH2$^+$ SH3$^+$, SH4$^+$ e.g., as detectable by flow cytometry, and CT-4$^+$, as detectable by RT-PCR. In another specific embodiment, the isolated placental stem cells are CD10$^+$, CD29$^+$, CD34$^-$, CD38$^-$, CD44$^+$, CD45$^-$, CD54$^+$, CD90$^+$ HLA-G$^-$, SH2$^+$, SH3$^+$ SH4$^+$, e.g., as detectable by flow cytometry. In another specific embodiment, the isolated placental stem cells are OCT-4$^+$ as detectable by RT-PCR, and ABC-p$^+$ as detectable by flow cytometry. In another specific embodiment, the isolated placental stem cells are SH2$^+$ SH3$^+$, SH4$^+$ as detectable by flow cytometry and CT-4$^+$ as detectable by flow cytometry. In another embodiment, the isolated placental stem cells are OCT-4$^+$ as detectable by RT-PCR, and CD34$^-$, SSEA3$^-$, and SSEA4$^-$ as detectable by RT-PCR. In a specific embodiment, said isolated OCT-4$^+$, CD34$^-$, SSEA3$^-$, and SSEA4$^-$ placental stem cells are additionally CD10$^+$, CD29$^+$, CD34$^-$, CD44$^+$, CD45$^-$, CD54$^+$, CD90$^+$ SH2$^+$, SH3$^+$ and SH4$^+$ as detectable by flow cytometry. In another specific embodiment, the isolated placental stem cells are OCT-4$^+$ as detectable by RT-PCR and CD34$^-$, and either SH3$^+$ or SH4$^+$ as detectable by flow cytometry. In another embodiment, the isolated placental stem cells are CD34$^-$ and either CD10$^+$, CD29$^+$, CD44$^+$, CD54$^+$, CD90$^+$ or OCT-4$^+$.

In another embodiment, isolated placental stem cells are CD200$^+$ as detectable by flow cytometry and OCT-4$^+$ as detectable by RT-PCR. In a specific embodiment, the isolated placental stem cells are CD73$^+$ and CD105$^+$ as detectable by flow cytometry. In another specific embodiment, said isolated placental stem cells are HLA-G$^-$. In another specific embodiment, said isolated CD200$^+$ CT-4$^+$ placental stem cells are CD34$^-$, CD38$^-$ or CD45$^-$ as detectable by flow cytometry. In another specific embodiment, said isolated CD200$^+$ CT-4$^+$ placental stem cells are CD34$^-$, CD38$^-$ and CD45$^-$ as detectable by flow cytometry. In another specific embodiment, said isolated CD200$^+$ CT-4$^+$ placental stem cells are CD34$^-$, CD38$^-$, CD45$^-$, CD73$^+$, CD105$^+$ and HLA-G$^-$ as detectable by flow cytometry. In another specific embodiment, the isolated CD200$^+$ CT-4$^+$ placental stem cells facilitate the production of one or more embryoid-like bodies by a population of placental cells that comprises the placental stem cells, when the population is cultured under conditions that allow the formation of embryoid-like bodies. In another specific embodiment, said isolated CD200$^+$ CT-4$^+$ placental stem cells are isolated away from placental cells that are not said placental stem cells. In another specific embodiment, said isolated CD200$^+$ CT-4$^+$ placental stem cells are isolated away from placental cells that do not display these characteristics.

In another embodiment, a cell population useful in the methods and compositions described herein is a population of cells comprising, e.g., that is enriched for, CD200$^+$ CT-4$^+$ placental stem cells, e.g., as detectable by flow cytometry and RT-PCR, respectively. In certain embodiments, at least about 10%, at least about 20%, at least about 30%, at least about 40%, at least about 50%, at least about 60%, at least about 70%. at least about 80%, at least about 90%, at least about 95%, or at least about 99% of cells in said cell population are isolated CD200$^+$ OCT-4$^+$ placental stem cells. In various embodiments, at least about 10%, at least about 20%, at least about 30%, at least about 40%, at least about 50%, or at least about 60% of cells in said cell population are isolated CD200$^+$, OCT-4$^+$ placental stem cells. In another embodiment, at least about 70% of said cells are said isolated CD200$^+$ OCT-4$^+$ placental stem cells. In another embodiment, at least about 80%, 90%, 95%, or 99% of cells in said cell population are said isolated CD200$^+$, OCT-4$^+$ placental stem cells. In a specific embodiment of the isolated populations, said isolated CD200$^+$ OCT-4$^+$ placental stem cells are additionally CD73$^+$ and CD105$^+$ as detectable by flow cytometry. In another specific embodiment, said isolated CD200$^+$, OCT-4$^+$ placental stem cells are additionally HLA-G$^-$ as detectable by flow cytometry. In another specific embodiment, said isolated CD200$^+$ OCT-4$^+$ placental stem cells are additionally CD34$^-$, CD38$^-$ and CD45$^-$ as detectable by flow cytometry. In another specific embodiment, said isolated CD200$^+$, OCT-4$^+$ placental stem cells are additionally CD34$^-$, CD38$^-$, CD45$^-$, CD73$^+$, CD105$^+$ and HLA-G$^-$ as detectable by flow cytometry. In another specific embodiment, said cell population is isolated away from placental cells that are not isolated CD200$^+$ OCT-4$^+$ placental cells. In another specific embodiment, said cell population is isolated away from placental cells that do not display these markers.

In another embodiment, the isolated placental stem cells useful in the methods and compositions described herein are CD73$^+$, CD105$^+$ and HLA-G$^-$ as detectable by flow cytometry. In another specific embodiment, the isolated CD73$^+$, CD105$^+$ and HLA-G$^-$ placental stem cells are additionally CD34$^-$, CD38$^-$ or CD45$^-$ as detectable by flow cytometry. In another specific embodiment, the isolated CD73$^+$, CD105$^+$ HLA-G$^-$ placental stem cells are additionally CD34$^-$, CD38$^-$ and CD45$^-$ as detectable by flow cytometry. In another specific embodiment, the isolated CD73$^+$, CD105$^+$ HLA-G$^-$ placental stem cells are additionally OCT-4$^+$ as detectable by RT-PCR. In another specific embodiment, the isolated CD73$^+$, CD105$^+$ HLA-G$^-$ placental stem cells are additionally CD200$^+$ as detectable by flow cytometry. In another specific embodiment, the isolated CD73$^+$, CD105$^+$, HLA-G$^-$ placental stem cells are additionally CD34$^-$, CD38$^-$, CD45$^-$, OCT-4$^+$ and CD200$^+$ as detectable by flow cytometry. In another specific embodiment, said the isolated CD73$^+$, CD105$^+$ HLA-G$^-$ placental stem cells are isolated away from placental cells that are not the isolated $CD73^+$, $CD105^+$ $HLA-G^-$ placental stem cells. In another specific embodiment, said the isolated $CD73^+$, $CD105^+$ $HLA-G^-$ placental stem cells are isolated away from placental cells that do not display these markers.

In another embodiment, a cell population useful in the methods and compositions described herein is a population of cells comprising, e.g., that is enriched for, isolated $CD73^+$, $CD105^+$ and $HLA-G^-$ placental stem cells, e.g., as detectable by flow cytometry. In certain embodiments, at least about 10%, at least about 20%, at least about 30%, at least about 40%, at least about 50%, at least about 60%, at least about 70%. at least about 80%, at least about 90%, at least about 95%, or at least about 99% of cells in said cell population are isolated $CD73^+$, $CD105^+$ $HLA-G^-$ placental stem cells. In various embodiments, at least about 10%, at least about 20%, at least about 30%, at least about 40%, at least about 50%, or at least about 60% of cells in said population of cells are isolated $CD73^+$, $CD105^+$ $HLA-G^-$ placental stem cells. In another embodiment, at least about 70% of cells in said population of cells are isolated $CD73^+$, $CD105^+$ $HLA-G^-$ placental stem cells. In another embodiment, at least about 80%, 90%, 95% or 99% of cells in said population of cells are isolated $CD73^+$, $CD105^+$, $HLA-G^-$ placental stem cells. In a specific embodiment of the above populations, said isolated $CD73^+$, $CD105^+$, $HLA-G^-$ placental stem cells are additionally $CD34^-$, $CD38^-$ or $CD45^-$ as detectable by flow cytometry. In another specific embodiment, said isolated $CD73^+$, $CD105^+$, $HLA-G^-$ placental stem cells are additionally $CD34^-$, $CD38^-$ and $CD45^-$ as detectable by flow cytometry. In another specific embodiment, said isolated $CD73^+$, $CD105^+$, $HLA-G^-$ placental stem cells are additionally $OCT-4^+$ as detectable by RT-PCR. In another specific embodiment, said isolated $CD73^+$, $CD105^+$, $HLA-G^-$ placental stem cells are additionally $CD200^+$ as detectable by flow cytometry. In another specific embodiment, said isolated $CD73^+$, $CD105^+$, $HLA-G^-$ placental stem cells are additionally $CD34^-$, $CD38^-$, $CD45^-$, and $CD200^+$ as detectable by flow cytometry, and $OCT-4^+$ as detectable by RT-PCR. In another specific embodiment, said cell population is isolated away from placental cells that are not $CD73^+$, $CD105^+$, $HLA-G^-$ placental cells. In another specific embodiment, said cell population is isolated away from placental cells that do not display these markers.

In another embodiment, the isolated placental stem cells useful in the methods and compositions described herein are isolated $HLA-A,B,C^+$, $CD45^-$, $CD133^-$ and $CD34^-$ placental stem cells, as detectable by flow cytometry. In another embodiment, a cell population useful in the methods and compositions described herein is a population of cells comprising isolated placental stem cells, wherein at least about 70%, at least about 80%, at least about 90%, at least about 95%, or at least about 99% of cells in said population of cells are isolated $HLA-A,B,C^+$, $CD45^-$, $CD133^-$ and $CD34^-$ placental stem cells. In a specific embodiment, said isolated placental cell or population of isolated placental cells is isolated away from placental cells that are not $HLA-A,B,C^+$, $CD45^-$, $CD133^-$ and $CD34^-$ placental stem cells. In another specific embodiment, said isolated placental stem cells are non-maternal in origin. In another specific embodiment, said population of isolated placental stem cells are substantially free of maternal components; e.g., at least about 40%, 45%, 50%, 55%, 60%, 65%, 70%, 75%, 80%, 85%, 90%, 95%, 98%, or 99% of said cells in said population of isolated placental stem cells are non-maternal in origin.

In another embodiment, the isolated placental stem cells useful in the methods and compositions described herein are isolated $CD10^+$, $CD13^+$, $CD33^+$, $CD45^-$, $CD117^-$ and $CD133^-$ cells, as detectable by flow cytometry. In another embodiment, a cell population useful in the methods and compositions described herein is a population of cells comprising isolated placental stem cells, wherein at least about 70%, at least about 80%, at least about 90%, at least about 95%, or at least about 99% of cells in said population of cells are isolated $CD10^+$, $CD13^+$, $CD33^+$, $CD45^-$, $CD117^-$ and $CD133^-$ placental stem cells, e.g., as detected by flow cytometry. In a specific embodiment, said isolated placental stem cells or population of isolated placental stem cells is isolated away from placental cells that are not said isolated placental stem cells. In another specific embodiment, said isolated $CD10^+$, $CD13^+$, $CD33^+$, $CD45^-$, $CD117^-$ and $CD133^-$ placental stem cells are non-maternal in origin, i.e., have the fetal genotype. In another specific embodiment, at least about 40%, 45%, 50%, 55%, 60%, 65%, 70%, 75%, 80%, 85%, 90%, 95%, 98%, or 99% of said cells in said population of isolated placental stem cells, are non-maternal in origin. In another specific embodiment, said isolated placental stem cells or population of isolated placental stem cells are isolated away from placental cells that do not display these characteristics.

In another embodiment, the isolated placental stem cells are isolated $CD10^+$, $CD33^-$, $CD44^+$, $CD45^-$, and $CD117^-$ placental cells, as detectable by flow cytometry. In another embodiment, a cell population useful for the in the methods and compositions described herein is a population of cells comprising, e.g., enriched for, isolated placental cells, wherein at least about 70%, at least about 80%, at least about 90%, at least about 95%, or at least about 99% of cells in said population of cells are isolated $CD10^+$, $CD33^-$, $CD44^+$, $CD45^-$, and $CD117^-$ placental cells. In a specific embodiment, said isolated placental cell or population of isolated placental cells is isolated away from placental cells that are not said cells. In another specific embodiment, said isolated placental cells are non-maternal in origin. In another specific embodiment, at least about 40%, 45%, 50%, 55%, 60%, 65%, 70%, 75%, 80%, 85%, 90%, 95%, 98%, or 99% of said placental stem cells in said cell population are non-maternal in origin. In another specific embodiment, said isolated placental stem cells or population of isolated placental stem cells is isolated away from placental cells that do not display these markers.

In another embodiment, the isolated placental stem cells useful in the methods and compositions described herein are isolated $CD10^+$, $CD13^-$, $CD33^-$, $CD45^-$, and $CD117^-$ placental stem cells. In another embodiment, a cell population useful in the methods and compositions described herein is a population of cells comprising, e.g., enriched for, isolated $CD10^+$, $CD13^-$, $CD33^-$, $CD45^-$, and $CD117^-$ placental stem cells, wherein at least about 70%, at least about 80%, at least about 90%, at least about 95%, or at least about 99% of cells in said population are CD10+ $CD13^-$, $CD33^-$, $CD45^-$, and $CD117^-$ placental stem cells. In a specific embodiment, said isolated placental stem cells or population of isolated placental stem cells are isolated away from placental cells that are not said placental stem cells. In another specific embodiment, said isolated placental cells are non-maternal in origin. In another specific embodiment, at least about 40%, 45%, 50%, 55%, 60%, 65%, 70%, 75%, 80%, 85%, 90%, 95%, 98%, or 99% of said cells in said cell population are non-maternal in origin. In another specific embodiment, said isolated placental stem cells or population of isolated placental stem cells is isolated away from placental cells that do not display these characteristics.

In another embodiment, the isolated placental stem cells useful in the methods and compositions described herein are HLA A,B,C+, CD45−, CD34−, and CD133−, and are additionally CD10+, CD13+, CD38−, CD44+, CD90+, CD105+, CD200+ and/or HLA-G−, and/or negative for CD117. In another embodiment, a cell population useful in the methods described herein is a population of cells comprising isolated placental stem cells, wherein at least about 20%, 25%, 30%, 35%, 40%, 45%, 50%, 55%, 60%, 65%, 70%, 75%, 80%, 85%, 90%, 95%, 98%, or about 99% of the cells in said population are isolated placental stem cells that are HLA A,B,C−, CD45−, CD34−, CD133−, and that are additionally positive for CD10, CD13, CD38, CD44, CD90, CD105, CD200, and/or negative for CD117 and/or HLA-G. In a specific embodiment, said isolated placental stem cells or population of isolated placental stem cells are isolated away from placental cells that are not said placental stem cells. In another specific embodiment, said isolated placental stem cells are non-maternal in origin. In another specific embodiment, at least about 40%, 45%, 50%, 55%, 60%, 65%, 70%, 75%, 80%, 85%, 90%, 95%, 98%, or 99% of said placental stem cells in said cell population are non-maternal in origin. In another specific embodiment, said isolated placental stem cells or population of isolated placental stem cells are isolated away from placental cells that do not display these characteristics.

In another embodiment, the isolated placental stem cells are isolated placental stem cells that are CD200+ and CD10+, as determined by antibody binding, and CD117−, as determined by both antibody binding and RT-PCR. In another embodiment, the isolated placental stem cells are isolated placental stem cells that are CD10+, CD29−, CD54+, CD200+, HLA-G−, MHC class I+ and β-2-microglobulin+. In another embodiment, isolated placental stem cells useful in the methods and compositions described herein are placental stem cells wherein the expression of at least one cellular marker is at least two-fold higher than in an equivalent number of mesenchymal stem cells, e.g., bone marrow-derived mesenchymal stem cells. In another specific embodiment, said isolated placental stem cells are non-maternal in origin. In another specific embodiment, at least about 40%, 45%, 50%, 55%, 60%, 65%, 70%, 75%, 80%, 85%, 90%, 95%, 98%, or 99% of said cells in said cell population are non-maternal in origin.

In another embodiment, the isolated placental stem cells are isolated placental stem cells that are one or more of CD10+, CD29+, CD44+, CD45−, CD54/ICAM+, CD62E−, CD62L−, CD62P−, CD80−, CD86−, CD103−, CD104−, CD105+, CD106/VCAM+, CD144/VE-cadherin$^{low}$, CD184/CXCR4−, β2-microglobulin$^{low}$, MHC-I−, MHC-II−, HLA-G$^{low}$, and/or PDL1$^{low}$. In a specific embodiment, the isolated placental stem cells are at least CD29+ and CD54+. In another specific embodiment, the isolated placental stem cells are at least CD44+ and CD106+. In another specific embodiment, the isolated placental stem cells are at least CD29+.

In another embodiment, a cell population useful in the methods and compositions described herein comprises isolated placental stem cells, and at least 50%, 60%, 70%, 80%, 90%, 95%, 98%, or 99% of the cells in said cell population are isolated placental stem cells that are one or more of CD10+, CD29+, CD44+, CD45−, CD54/ICAM+, CD62-E−, CD62-L−, CD62-P−, CD80−, CD86−, CD103−, CD104−, CD105+, CD106/VCAM+, CD144/VE-cadherin$^{dim}$, CD184/CXCR4−, β2-microglobulin$^{dim}$, HLA-I$^{dim}$, HLA-II−, HLA-G$^{dim}$, and/or PDL1$^{dim}$ placental stem cells. In another specific embodiment, at least 50%, 60%, 70%, 80%, 90%, 95%, 98%, or 99% of cells in said cell population are CD10+, CD29+, CD44+, CD45−, CD54/ICAM+, CD62-E−, CD62-L−, CD62-P−, CD80−, CD86−, CD103−, CD104−, CD105+, CD106/VCAM+, CD144/VE-cadherin$^{dim}$, CD184/CXCR4−, β2-microglobulin$^{dim}$, MHC-I$^{dim}$, MHC-II−, HLA-G$^{dim}$, and PDL1$^{dim}$ placental stem cells. In certain embodiments, the placental stem cells express HLA-II markers when induced by interferon gamma (IFN-γ).

In another embodiment, the isolated placental stem cells useful in the methods and compositions described herein are isolated placental stem cells that are one or more, or all, of CD10+, CD29+, CD34−, CD38−, CD44+, CD45−, CD54+, CD90', SH2+ SH3+, SH4+ SSEA3−, SSEA4−, OCT-4+, and ABC-p+, where ABC-p is a placenta-specific ABC transporter protein (also known as breast cancer resistance protein (BCRP) or as mitoxantrone resistance protein (MXR)), wherein said isolated placental stem cells are obtained by perfusion of a mammalian, e.g., human, placenta that has been drained of cord blood and perfused to remove residual blood.

In another specific embodiment of any of the above embodiments, expression of the recited cellular marker(s) (e.g., cluster of differentiation or immunogenic marker(s)) is determined by flow cytometry. In another specific embodiment, expression of the marker(s) is determined by RT-PCR.

Gene profiling can be used to confirm that isolated placental stem cells, and populations of isolated placental stem cells, are distinguishable from other cells, e.g., mesenchymal stem cells, e.g., bone marrow-derived mesenchymal stem cells. The isolated placental stem cells described herein can be distinguished from, e.g., bone marrow-derived mesenchymal stem cells on the basis of the expression of one or more genes, the expression of which is specific to placental stem cells or umbilical cord stem cells in comparison to bone marrow-derived mesenchymal stem cells, e.g., the expression of which is significantly higher in the isolated placental stem cells in comparison to bone marrow-derived mesenchymal stem cells. In particular, the isolated placental stem cells, useful in the methods of treatment provided herein, can be distinguished from bone marrow-derived mesenchymal stem cells on the basis of the expression of one or more genes, the expression of which is detectably higher (e.g., at least twofold, threefold higher, fourfold higher, fivefold higher, or more) in the isolated placental stem cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Pat. No. 8,057,788, the disclosure of which is incorporated herein by reference in its entirety, especially Example 10. In a specific embodiment, the isolated placental stem cells, useful in the methods of treatment provided herein, express genes at a detectably higher level than an equivalent number of bone marrow-derived mesenchymal stem cells; wherein said genes comprise ELOVL2, ST3GAL6, ST6GALNAC5, or SLC12A8. In a specific embodiment, said genes comprise ARTS-1, IER3, IL6, KRT18, LRAP, MEST, NFE2L3, or TGFB2. In a specific embodiment, said genes comprise CPA4, TCF21, VTN, FLJ10781, or NUAK1. In a specific embodiment, said genes comprise CD200. In certain specific embodiments, said expression of said one or more genes is determined, e.g., by RT-PCR or microarray analysis, e.g., using a U133-A microarray (Affymetrix).

In some embodiments, said isolated placental stem cells express said genes at a level detectably higher level than an equivalent number of bone marrow-derived mesenchymal stem cells over about 3 to about 35 population doublings. In a specific embodiment, said isolated placental stem cells express said genes at a level detectably higher level than an equivalent number of bone marrow-derived mesenchymal stem cells over 3 population doublings. In a specific embodiment, said isolated placental stem cells express said genes at a level detectably higher level than an equivalent number of bone marrow-derived mesenchymal stem cells over 11-14 population doublings. In a specific embodiment, said isolated placental stem cells express said genes at a level detectably higher than an equivalent number of bone marrow-derived mesenchymal stem cells over 24-38 population doublings.

In a specific embodiment, said isolated placental stem cells can express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In one embodiment, said medium additionally comprises MCDB-201 (chick fibroblast basal medium).

Specific sequences for these genes can be found in GenBank at Accession Nos. NM_001615 (ACTG2), BC065545 (ADARB1), (NM_181847 (AMIGO2), AY358590 (ARTS-1), BC074884 (B4GALT6), BC008396 (BCHE), BCO20196 (C11orf9), BCO31103 (CD200), NM_001845 (COL4A1), NM_001846 (COL4A2), BCO52289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BCO23312 (ST3GAL6), BC001201 (ST6GALNAC5), BC126160 or BC065328 (SLC12A8), BCO25697 (TCF21), BC096235 (TGFB2), BC005046 (VTN), and BC005001 (ZC3H12A) as of March 2008.

In certain specific embodiments, said isolated placental stem cells express one or more of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than a bone marrow-derived mesenchymal stem cell, when the cells are grown under equivalent conditions.

In a more specific embodiment, said isolated placental stem cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In certain embodiments, a population of isolated placental stem cells useful in the methods and compositions described herein express one or more genes at a detectably higher level than a population of bone marrow-derived mesenchymal stem cells, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said population of bone marrow derived stem cells has undergone a number of passages in culture equivalent to the number of passages said placental stem cell has undergone, and wherein said population of bone marrow-derived mesenchymal stem cells has a number of cells equivalent to said population of isolated stem cells. In a more specific embodiment, the population of isolated placental stem cells expresses ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than said population of isolated bone marrow-derived mesenchymal stem cells.

In specific embodiments, the placental stem cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells wherein said bone marrow-derived mesenchymal stem cells have undergone a number of passages in culture equivalent to the number of passages said isolated placental stem cells have undergone. In other specific embodiments, the placental stem cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells, wherein said bone marrow-derived mesenchymal stem cells have undergone a number of passages in culture equivalent to the number of passages said isolated placental stem cells have undergone.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental stem cells, to identify a population of cells as comprising at least a plurality of isolated placental stem cells, or the like. Populations of isolated placental stem cells, the identity of which is confirmed, can be clonal, e.g., populations of isolated placental stem cells expanded from a single isolated placental stem cells, or a mixed population of placental stem cells, e.g., a population of cells comprising isolated placental stem cells that are expanded from multiple isolated placental stem cells, or a population of cells comprising isolated placental stem cells, as described herein, and at least one other type of cell.

The level of expression of these genes can be used to select populations of isolated placental stem cells. For example, a population of cells, e.g., clonally-expanded placental stem cells, may be selected if the expression of one or more of the genes listed above is significantly higher in a sample from the population of cells than in an equivalent population of bone marrow-derived mesenchymal stem cells. Such selecting can be of a population from a plurality of isolated placental stem cell populations, from a plurality of cell populations, the identity of which is not known, etc.

Isolated placental stem cells can be selected on the basis of the level of expression of one or more such genes as compared to the level of expression in said one or more genes in, e.g., a bone marrow-derived mesenchymal stem cell control. In one embodiment, the level of expression of said one or more genes in a sample comprising an equivalent number of bone marrow-derived mesenchymal stem cells is used as a control. In another embodiment, the control, for isolated placental stem cells tested under certain conditions, is a numeric value representing the level of expression of said one or more genes in bone marrow-derived mesenchymal stem cells under said conditions.

For example, in some embodiments, a method for selecting isolated placental stem cells or populations of isolated placental stem cells on the basis of gene expression of one or more genes comprises selecting cells that express one or more genes at a detectably higher level than a bone marrow-derived mesenchymal stem cell, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow derived stem cell has undergone a number of passages in culture equivalent to the number of passages said placental stem cell has undergone. In a more specific embodiment, said selecting comprises selecting cells that express ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN and ZC3H12A at a detectably higher level than a bone marrow-derived mesenchymal stem cell.

The isolated placental stem cells described herein can display the above characteristics (e.g., combinations of cell surface markers and/or gene expression profiles) in primary culture, or during culture in medium comprising, e.g., DMEM-LG (Gibco), 2% fetal calf serum (FCS) (Hyclone Laboratories), 1× insulin-transferrin-selenium (ITS), 1× linoleic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

In certain embodiments of any of the placental stem cells disclosed herein, the cells are human. In certain embodiments of any of the placental cells disclosed herein, the cellular marker characteristics or gene expression characteristics are human markers or human genes.

In another specific embodiment of the isolated placental stem cells or populations of cells comprising the isolated placental stem cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38, or 40 population doublings. In a specific embodiment of the isolated placental stem cells or populations of cells comprising the isolated placental stem cells, said cells or population have been passaged at least, about, or no more than 3 times, 4 times, 5 times, or 6 times. In a specific embodiment of the isolated placental stem cells or populations of cells comprising the isolated placental stem cells, said cells or population have been passaged at least, about, or no more than 3-10 times, 4-8 times, or 5-7 times. In a specific embodiment of the isolated placental stem cells or populations of cells comprising the isolated placental stem cells, said cells or population have been proliferated for at least, about, or no more than, 2, 3, 4, 5, or 6 population doublings. In a specific embodiment of the isolated placental stem cells or populations of cells comprising the isolated placental stem cells, said cells or population have been proliferated for at least, about, or no more than, 3-10, 4-8, or 5-7 population doublings. In a specific embodiment of the isolated placental stem cells or populations of cells comprising the isolated placental stem cells, said cells or population have been proliferated for at least, about, or no more than, 6-10, 11-14, 15-30, 30-45, or 18-26, or 24-38 population doublings. In another specific embodiment of said isolated placental stem cells or populations of cells comprising the isolated placental stem cells, said cells or population are primary isolates. In another specific embodiment of the isolated placental stem cells, or populations of cells comprising isolated placental stem cells, that are disclosed herein, said isolated placental stem cells are fetal in origin (that is, have the fetal genotype).

In certain embodiments, said isolated placental stem cells do not differentiate during culturing in growth medium, i.e., medium formulated to promote proliferation, e.g., during proliferation in growth medium. In another specific embodiment, said isolated placental stem cells do not require a feeder layer in order to proliferate. In another specific embodiment, said isolated placental stem cells do not differentiate in culture in the absence of a feeder layer, solely because of the lack of a feeder cell layer.

In another embodiment, the isolated placental cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, between about 3% and about 25% of placental stem cells are positive for ALDH. In another embodiment, said isolated placental stem cells show at least three-fold, or at least five-fold, higher ALDH activity than a population of bone marrow-derived mesenchymal stem cells having about the same number of cells and cultured under the same conditions.

In certain embodiments of any of the populations of cells comprising the isolated placental stem cells described herein, the placental stem cells in said populations of cells are substantially free of cells having a maternal genotype; e.g., at least 40%, 45%, 50%, 55%, 60%, 65%, 70%, 75%, 80%, 85%, 90%, 95%, 98%, or 99% of the placental stem cells in said population have a fetal genotype. In certain other embodiments of any of the populations of cells comprising the isolated placental stem cells described herein, the populations of cells comprising said placental stem cells are substantially free of cells having a maternal genotype; e.g., at least 40%, 45%, 50%, 55%, 60%, 65%, 70%, 75%, 80%, 85%, 90%, 95%, 98%, or 99% of the cells in said population have a fetal genotype.

In a specific embodiment of any of the above isolated placental stem cells or cell populations comprising isolated placental stem cells, the karyotype of the cells, e.g., all of the cells, or at least about 95% or about 99% of the cells in said population, is normal. In another specific embodiment of any of the above placental stem cells or populations or placental stem cells, the placental stem cells are non-maternal in origin.

In a specific embodiment of any of the embodiments of placental cells disclosed herein, the placental cells are genetically stable, displaying a normal diploid chromosome count and a normal karyotype.

Isolated placental stem cells, or populations of isolated placental stem cells, bearing any of the above combinations of markers, can be combined in any ratio. Any two or more of the above isolated placental stem cell populations can be combined to form an isolated placental stem cell population. For example, a population of isolated placental stem cells can comprise a first population of isolated placental stem cells defined by one of the marker combinations described above, and a second population of isolated placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental stem cells or isolated placental stem cell populations can be combined.

Isolated placental stem cells useful in the methods and compositions described herein can be obtained, e.g., by disruption of placental tissue, with or without enzymatic digestion (see Section 4.4.3) or perfusion (see Section 4.4.4). For example, populations of isolated placental stem cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental stem cells; and isolating said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental stem cells, contained within a population of cells obtained from perfusion of a placenta, are at least 50%, 60%, 70%, 80%, 90%, 95%, 99%, or at least 99.5% of said population of placental stem cells. In another specific embodiment, the isolated placental stem cells collected by perfusion comprise fetal and maternal cells. In another specific embodiment, the isolated placental stem cells collected by perfusion are at least 50%, 60%, 70%, 80%, 90%, 95%, 99%, or at least 99.5% fetal cells.

In another specific embodiment, provided herein is a composition comprising a population of the isolated placental stem cells, as described herein, collected (isolated) by perfusion, wherein said composition comprises at least a portion of the perfusion solution used to isolate the placental stem cells.

Populations of the isolated placental stem cells described herein can be produced by digesting placental tissue with a tissue-disrupting enzyme to obtain a population of placental cells comprising the placental stem cells, and isolating, or substantially isolating, a plurality of the placental stem cells from the remainder of said placental cells. The whole, or any part of, the placenta can be digested to obtain the isolated placental stem cells described herein. In specific embodiments, for example, said placental tissue can be a whole placenta (e.g., including an umbilical cord), an amniotic membrane, chorion, a combination of amnion and chorion, or a combination of any of the foregoing. In other specific embodiments, the tissue-disrupting enzyme is trypsin or collagenase. In various embodiments, the isolated placental stem cells, contained within a population of cells obtained from digesting a placenta, are at least 50%, 60%, 70%, 80%, 90%, 95%, 99%, or at least 99.5% of said population of placental cells.

The populations of isolated placental stem cells described above, and populations of isolated placental stem cells generally, can comprise about, at least, or no more than, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{19}$, $5 \times 10^{19}$, $1 \times 10^{11}$ or more of the isolated placental stem cells. Populations of isolated placental stem cells useful in the methods of treatment described herein comprise at least 50%, 55%, 60%, 65%, 70%, 75%, 80%, 85%, 90%, 95%, 98%, or 99% viable isolated placental stem cells, e.g., as determined by, e.g., trypan blue exclusion.

For any of the above placental stem cells, or populations of placental stem cells, the cells or population of placental stem cells are, or can comprise, cells that have been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38, or 40 population doublings, or more.

In a specific embodiment of any of the above placental stem cells or placental stem cell populations, the karyotype of the cells, or at least about 95% or about 99% of the cells in said population, is normal. In another specific embodiment of any of the above placental stem cells or placental stem cell populations, the cells, or cells in the population of cells, are non-maternal in origin.

Isolated placental stem cells, or populations of isolated placental stem cells, bearing any of the above combinations of markers, can be combined in any ratio. Any two or more of the above placental stem cell populations can be isolated, or enriched, to form a placental stem cell population. For example, a population of isolated placental stem cells comprising a first population of placental stem cells defined by one of the marker combinations described above can be combined with a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cell populations can be combined.

In a specific embodiment of the above-mentioned placental stem cells, the placental stem cells constitutively secrete IL-6, IL-8 and monocyte chemoattractant protein (MCP-1).

The populations of placental cells described above can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

In certain embodiments, the placental stem cells useful in the methods provided herein, do not express CD34, as detected by immunolocalization, after exposure to 1 to 100 ng/mL VEGF for 4 to 21 days. In a specific embodiment, said placental stem cells are adherent to tissue culture plastic. In another specific embodiment, said placental stem cells induce endothelial cells to form sprouts or tube-like structures, e.g., when cultured in the presence of an angiogenic factor such as vascular endothelial growth factor (VEGF), epithelial growth factor (EGF), platelet derived growth factor (PDGF) or basic fibroblast growth factor (bFGF), e.g., on a substrate such as MATRIGEL™.

In another aspect, the placental stem cells provided herein, or a population of cells, e.g., a population of placental stem cells, or a population of cells wherein at least about 50%, 60%, 70%, 80%, 90%, 95%, or 98% of cells in said population of cells are placental stem cells, secrete one or more, or all, of VEGF, HGF, IL-8, MCP-3, FGF2, follistatin, G-CSF, EGF, ENA-78, GRO, IL-6, MCP-1, PDGF-BB, TIMP-2, uPAR, or galectin-1, e.g., into culture medium in which the cell, or cells, are grown. In another embodiment, the placental stem cells express increased levels of CD202b, IL-8 and/or VEGF under hypoxic conditions (e.g., less than about 5% $O_2$) compared to normoxic conditions (e.g., about 20% or about 21% $O_2$).

In another embodiment, any of the placental stem cells or populations of cells comprising placental stem cells described herein can cause the formation of sprouts or tube-like structures in a population of endothelial cells in contact with or proximity to said placental stem cells. In a specific embodiment, the placental stem cells are co-cultured with human endothelial cells, which form sprouts or tube-like structures, or support the formation of endothelial cell sprouts, e.g., when cultured in the presence of extracellular matrix proteins such as collagen type I and IV, and/or angiogenic factors such as vascular endothelial growth factor (VEGF), epithelial growth factor (EGF), platelet derived growth factor (PDGF) or basic fibroblast growth factor (bFGF), e.g., in or on a substrate such as placental collagen or MATRIGEL™ for at least 4 days. In another embodiment, any of the populations of cells comprising placental stem cells, described herein, secrete angiogenic factors such as vascular endothelial growth factor (VEGF), hepatocyte growth factor (HGF), platelet derived growth factor (PDGF), basic fibroblast growth factor (bFGF), or Interleukin-8 (IL-8) and thereby can induce human endothelial cells to form sprouts or tube-like structures when cultured in the presence of extracellular matrix proteins such as collagen type I and IV e.g., in or on a substrate such as placental collagen or MATRIGEL™.

In another embodiment, any of the above populations of cells comprising placental stem cells secretes angiogenic factors. In specific embodiments, the population of cells secretes vascular endothelial growth factor (VEGF), hepatocyte growth factor (HGF), platelet derived growth factor (PDGF), basic fibroblast growth factor (bFGF), and/or interleukin-8 (IL-8). In other specific embodiments, the population of cells comprising placental stem cells secretes one or more angiogenic factors and thereby induces human endothelial cells to migrate in an in vitro wound healing assay. In other specific embodiments, the population of cells comprising placental stem cells induces maturation, differentiation or proliferation of human endothelial cells, endothelial progenitors, myocytes or myoblasts.

4.3.3 Selecting and Producing Placental Cell Populations

In certain embodiments, populations of placental stem cells can be selected, wherein the population is immunosuppressive. In one embodiment, for example, immunosuppressive placental stem cells can be selected from a plurality of placental cells, comprising selecting a population of placental cells wherein at least 10%, at least 20%, at least 30%, at least 40%, at least 50%, at least 60%, at least 70%, at least 80%, at least 90%, or at least 95% of said cells are $CD10^+$, $CD34^-$, $CD105^+$ placental stem cells, $CD10^+$, $CD34^-$, $CD200^+$ placental stem cells, or $CD10^+$, $CD34^-$, $CD105^+$, $CD200^+$ placental stem cells, and wherein said placental stem cells detectably suppress T cell proliferation in a mixed lymphocyte reaction (MLR) assay. In a specific embodiment, said selecting comprises selecting placental stem cells that are also $CD45^-$ and $CD90^-$.

In another embodiment, provided herein is a method of selecting a plurality of immunosuppressive placental stem cells from a plurality of placental cells, comprising selecting a population of placental stem cells wherein at least 10%, at least 20%, at least 30%, at least 40%, at least 50%, at least 60%, at least 70%, at least 80%, at least 90%, or at least 95% of said cells are $CD200^+$, $HLA-G^-$ placental stem cells, and wherein said placental stem cells detectably suppress T cell proliferation in a mixed lymphocyte reaction (MLR) assay. In a specific embodiment, said selecting comprises selecting placental stem cells that are also $CD73^+$ and $CD105^+$. In another specific embodiment, said selecting comprises selecting placental stem cells that are also $CD34^-$, $CD38^-$ or $CD45^-$. In another specific embodiment, said selecting comprises selecting placental stem cells that are also $CD34^-$, $CD38^-$, $CD45^-$, $CD73^+$ and $CD105^+$. In another specific embodiment, said selecting also comprises selecting a plurality of placental cells, e.g., the placental stem cells described above, that forms one or more embryoid-like bodies when cultured under conditions that allow the formation of embryoid-like bodies.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50%, at least 60%, at least 70%, at least 80%, at least 90%, or at least 95% of said cells are CD73$^+$, CD105$^+$, CD200$^+$ placental stem cells, and wherein said placental cells detectably suppress T cell proliferation in a mixed lymphocyte reaction (MLR) assay. In a specific embodiment, said selecting comprises selecting placental stem cells that are also HLA-G$^-$. In another specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, and HLA-G$^-$. In another specific embodiment, said selecting additionally comprises selecting a population of placental stem cells that produces one or more embryoid-like bodies when the population is cultured under conditions that allow the formation of embryoid-like bodies.

In another embodiment, also provided herein is a method of selecting a plurality of immunosuppressive placental stem cells from a plurality of placental cells, comprising selecting a plurality of placental cells wherein at least 10%, at least 20%, at least 30%, at least 40%, at least 50%, at least 60%, at least 70%, at least 80%, at least 90%, or at least 95% of said cells are CD200$^+$, OCT-4$^+$ placental stem cells, and wherein said placental cells detectably suppress T cell proliferation in a mixed lymphocyte reaction (MLR) assay. In a specific embodiment, said selecting comprises selecting placental stem cells that are also CD73$^+$ and CD105$^+$. In another specific embodiment, said selecting comprises selecting placental stem cells that are also HLA-G$^-$. In another specific embodiment, said selecting comprises selecting placental stem cells that are also CD34$^-$, CD38$^-$ and CD45$^-$. In another specific embodiment, said selecting comprises selecting placental stem cells that are also CD34$^-$, CD38$^-$, CD45$^-$, CD73$^+$, CD105$^+$ and HLA-G$^-$.

In another embodiment, provided herein is a method of selecting a plurality of immunosuppressive placental stem cells from a plurality of placental cells, comprising selecting a plurality of placental cells wherein at least 10%, at least 20%, at least 30%, at least 40%, at least 50%, at least 60%, at least 70%, at least 80%, at least 90%, or at least 95% of said cells are CD73$^+$, CD105$^+$ and HLA-G$^-$ placental stem cells, and wherein said placental cells detectably suppress T cell proliferation in a mixed lymphocyte reaction (MLR) assay. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also CD200$^+$. In another specific embodiment, said selecting comprises selecting placental stem cells that are also CD34$^-$, CD38$^-$, CD45$^-$, OCT-4$^+$ and CD200$^+$.

In another embodiment, also provided herein is provides a method of selecting a plurality of immunosuppressive placental stem cells from a plurality of placental cells, comprising selecting a plurality of placental cells wherein at least 10%, at least 20%, at least 30%, at least 40%, at least 50%, at least 60%, at least 70%, at least 80%, at least 90%, or at least 95% of said cells are CD73$^+$, CD105$^+$ placental stem cells, and wherein said plurality forms one or more embryoid-like bodies under conditions that allow formation of embryoid-like bodies. In a specific embodiment, said selecting comprises selecting placental stem cells that are also CD34$^-$, CD38$^-$ or CD45$^-$. In another specific embodiment, said selecting comprises selecting placental stem cells that are also CD34$^-$, CD38$^-$ and CD45$^-$. In another specific embodiment, said selecting comprises selecting placental stem cells that are also OCT-4$^+$. In a more specific embodiment, said selecting comprises selecting placental stem cells that are also OCT-4$^+$, CD34$^-$, CD38$^-$ and CD45$^-$.

In another embodiment, provided herein is a method of selecting a plurality of immunosuppressive placental stem cells from a plurality of placental cells, comprising selecting a plurality of placental stem cells wherein at least 10%, at least 20%, at least 30%, at least 40%, at least 50%, at least 60%, at least 70%, at least 80%, at least 90%, or at least 95% of said isolated placental cells are OCT4$^+$ placental stem cells, and wherein said plurality forms one or more embryoid-like bodies under conditions that allow formation of embryoid-like bodies. In a specific embodiment, said selecting comprises selecting placental stem cells that are also CD73$^+$ and CD105$^+$. In another specific embodiment, said selecting comprises selecting placental stem cells that are also CD34$^-$, CD38$^-$, or CD45$^-$. In another specific embodiment, said selecting comprises selecting placental stem cells that are also CD200'. In a more specific embodiment, said selecting comprises selecting placental stem cells that are also CD73$^+$, CD105$^+$, CD200$^+$, CD34$^-$, CD38$^-$, and CD45$^-$.

Immunosuppressive populations, or pluralities, of placental cells can be produced according to the methods provided herein. For example, provided herein is method of producing a cell population, comprising selecting any of the pluralities of placental stem cells described above, and isolating the plurality of placental cells from other cells, e.g., other placental cells. In a specific embodiment, provided herein is a method of producing a cell population comprising selecting placental stem cells, wherein said placental stem cells (a) adhere to a substrate; (b) express CD200 and do not express HLA-G; or express CD73, CD105, and CD200; or express CD200 and OCT-4; or express CD73, CD105, and do not express HLA-G; or express CD73 and CD105 and facilitate the formation of one or more embryoid-like bodies in a population of placental cells that comprise the placental stem cells, when said population is cultured under conditions that allow formation of embryoid-like bodies; or express OCT-4 and facilitate the formation of one or more embryoid-like bodies in a population of placental cells that comprise the placental stem cells, when said population is cultured under conditions that allow formation of embryoid-like bodies; and (c) detectably suppress CD4$^+$ or CD8$^+$ T cell proliferation in an MLR (mixed lymphocyte reaction) or regression assay; and selecting said placental stem cells, or isolating said placental stem cells from other cells to form a cell population.

In a more specific embodiment, immunosuppressive placental stem cell populations can be produced by a method comprising selecting placental stem cells that (a) adhere to a substrate, (b) express CD200 and do not express HLA-G, and (c) detectably suppress CD4$^+$ or CD8$^+$ T cell proliferation in an MLR (mixed lymphocyte reaction); and isolating said placental stem cells from other cells to form a cell population. In another specific embodiment, the method comprises selecting placental stem cells that (a) adhere to a substrate, (b) express CD73, CD105, and CD200, and (c) detectably suppress CD4$^+$ or CD8$^+$ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD200 and OCT-4, and (c) detectably suppress CD4$^+$ or CD8$^+$ T cell proliferation in an MLR; and isolating said placental stem cells from other cells to form a cell population. In another specific embodiment, provided herein is a method of producing a cell population comprising selecting placental stem cells that (a) adhere to a substrate, (b) express CD73 and CD105, (c) form embryoid-like bodies when cultured under conditions allowing the formation of embryoid-like bodies, and (d) detectably suppress CD4$^+$ or CD8$^+$ T cell proliferation in an MLR; and isolating said placental stem cells from other cells to form a cell population. In another specific embodiment, the method comprises selecting placental stem cells that (a) adhere to a substrate, (b) express CD73 and CD105, and do not express HLA-G, and (c) detectably suppress CD4$^+$ or CD8$^+$ T cell proliferation in an MLR; and isolating said placental stem cells from other cells to form a cell population. In another specific embodiment, the method comprises selecting placental stem cells that (a) adhere to a substrate, (b) express OCT-4, (c) form embryoid-like bodies when cultured under conditions allowing the formation of embryoid-like bodies, and (d) detectably suppress CD4$^+$ or CD8$^+$ T cell proliferation in an MLR; and isolating said placental cells from other cells to form a cell population.

In a specific embodiment of the methods of producing an immunosuppressive placental stem cell population, said T cells and said placental stem cells are present in said MLR at a ratio of about 5:1. The placental stem cells used in the method can be derived from the whole placenta, or primarily from amnion, or amnion and chorion. In another specific embodiment, the placental stem cells suppress CD4$^+$ or CD8$^+$ T cell proliferation by at least 50%, at least 75%, at least 90%, or at least 95% in said MLR compared to an amount of T cell proliferation in said MLR in the absence of said placental stem cells. The method can additionally comprise the selection and/or production of a placental stem cell population capable of immunomodulation, e.g., suppression of the activity of, other immune cells, e.g., an activity of a natural killer (NK) cell.

4.3.4 Growth in Culture

The growth of the placental cells, e.g., the placental stem cells described herein, as for any mammalian cell, depends in part upon the particular medium selected for growth. Under optimum conditions, placental stem cells typically double in number in 3-5 days. During culture, the placental stem cells provided herein adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells provided herein, when cultured under appropriate conditions, can form embryoid-like bodies, that is, three-dimensional clusters of cells that grow atop the adherent stem cell layer. Mesenchymal stem cells, e.g., bone marrow-derived mesenchymal stem cells, do not develop embryoid-like bodies in culture.

4.3.5 Differentiation

The placental cells, useful in the methods of treatment provided herein, in certain embodiments are differentiable into different committed cell lineages. For example, in certain embodiments, the placental cells can be differentiated into cells of an adipogenic, chondrogenic, neurogenic, or osteogenic lineage. Such differentiation can be accomplished, e.g., by any method known in the art for differentiating, e.g., bone marrow-derived mesenchymal stem cells into similar cell lineages, or by methods described elsewhere herein. Specific methods of differentiating placental cells into particular cell lineages are disclosed in, e.g., U.S. Pat. Nos. 7,311,905 and 8,057,788, the disclosures of which are hereby incorporated by reference in their entireties.

The placental stem cells provided herein can exhibit the capacity to differentiate into a particular cell lineage in vitro, in vivo, or in vitro and in vivo. In a specific embodiment, the placental stem cells provided herein can be differentiated in vitro when placed in conditions that cause or promote differentiation into a particular cell lineage, but do not detectably differentiate in vivo, e.g., in a NOD-SCID mouse model.

4.4 Methods of Obtaining Placental Stem Cells 4.4.1 Stem Cell Collection Composition Placental stem cells can be collected and isolated according to the methods provided herein or in any other method known in the art. Generally, placental stem cells are obtained from a mammalian placenta using a physiologically-acceptable solution, e.g., a stem cell collection composition. A stem cell collection composition is described in detail in related U.S. Provisional Application No. 60/754,969, entitled "Improved Composition for Collecting and Preserving Placental cells and Methods of Using the Composition" filed on Dec. 29, 2005.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl, etc.), a culture medium (e.g., DMEM, HDMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.), dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

4.4.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to placental stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

4.4.3 Physical Disruption and Enzymatic Digestion of Placental Tissue

In one embodiment, placental stem cells are collected from a mammalian placenta by physical disruption, e.g., enzymatic digestion, of the organ, e.g., using the stem cell collection composition described in Section 4.4.1, above. For example, the placenta, or a portion thereof, may be, e.g., crushed, sheared, minced, diced, chopped, macerated or the like, while in contact with, e.g., a buffer, medium or a stem cell collection composition, and the tissue subsequently digested with one or more enzymes. The placenta, or a portion thereof, may also be physically disrupted and digested with one or more enzymes, and the resulting material then immersed in, or mixed into, a buffer, medium or a stem cell collection composition. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

Typically, placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900, or about 1000 cubic millimeters in volume.

Enzymatic digestion can be performed using single enzymes or combinations of enzymes. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the placental stem cells with the stem cell collection composition.

It will be appreciated that where an entire placenta, or portion of a placenta comprising both fetal and maternal cells (for example, where the portion of the placenta comprises the chorion or cotyledons) is digested to obtain placental stem cells, the placental cells collected will comprise a mix of placental cells derived from both fetal and maternal sources. Where a portion of the placenta that comprises no, or a negligible number of, maternal cells (for example, amnion) is used to obtain placental stem cells, the placental stem cells collected will comprise almost exclusively fetal placental stem cells.

4.4.4 Placental Perfusion

Placental stem cells can also be obtained by perfusion of the mammalian placenta. Methods of perfusing mammalian placenta to obtain stem cells are disclosed, e.g., in Hariri, U.S. Pat. No. 7,045,148, and in related International Patent Application Publication No. WO 2007/079185.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood; this portion of the perfusion can be discarded. The perfusion fluid becomes more colorless as perfusion proceeds and the residual cord blood cells are washed out of the placenta.

The volume of perfusion liquid used to collect placental stem cells may vary depending upon the number of placental stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); or antibiotics such as streptomycin (e.g., at 40-100 µg/ml) or penicillin (e.g., at 40 U/ml); or amphotericin B (e.g., at 0.5 µg/ml)). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of placental stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where they are collectable, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Stem cells can be isolated from placenta by perfusion with a solution comprising one or more proteases or other tissue-disruptive enzymes. In a specific embodiment, a placenta or portion thereof is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental stem cells are washed after several minutes with a cold (e.g., 4° C.) stem cell collection composition described elsewhere herein.

Perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

4.4.5 Isolation, Sorting, and Characterization of Placental Cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means removing at least 20%, 30%, 40%, 50%, 60%, 70%, 80%, 90%, 95%, or 99% of the cells with which the placental stem cells are normally associated in the intact mammalian placenta.

Placental stem cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex).

In one embodiment of isolation of placental stem cells, aliquots of, for example, about 5-10×10$^6$ placental cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34 as compared to, for example, an isotype control; if so, the cell is CD34+. Likewise, if a cell produces enough OCT-4 RNA to be detectable by RT-PCR, or significantly more OCT-4 RNA than a terminally-differentiated cell, the cell is OCT-4$^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted, e.g., further isolated, using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, placental stem cells can be sorted on the basis of expression of the markers CD34, CD38, CD44, CD45, CD73, CD105, OCT-4 and/or HLA-G, or any of the other markers listed elsewhere herein. This can be accomplished in connection with procedures to select stem cells on the basis of their adherence properties in culture. For example, adherence selection of placental stem cells can be accomplished before or after sorting on the basis of marker expression. In one embodiment, for example, placental stem cells can be sorted first on the basis of their expression of CD34; CD34$^-$ cells are retained, and cells that are CD200$^+$ or HLA-G$^+$, are separated from all other CD34$^-$ cells. In another embodiment, placental stem cells can be sorted based on their expression of CD200 and/or HLA-G, or lack thereof; for example, cells displaying either of these markers can be isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental stem cells are sorted by expression, or lack thereof, of CD200, HLA-G, CD73, CD105, CD34, CD38 and CD45, and placental stem cells that are CD200$^+$, HLA-G$^-$, CD73$^+$, CD105$^+$, CD34$^-$, CD38$^-$ and CD45$^-$ are isolated from other placental cells for further use.

In another embodiment, magnetic beads can be used to separate cells, e.g., separate placental stem cells from other placental cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture can be isolated from other placental cells. In another embodiment, OCT-4$^+$ placental cells that produce one or more embryoid-like bodies in culture are isolated from other placental cells.

In another embodiment, placental stem cells can be identified and characterized by a colony forming unit assay. Colony forming unit assays are commonly known in the art, such as using MESENCULT™ medium (Stem Cell Technologies, Inc., Vancouver British Columbia).

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

4.5 Culture of Placental Stem Cells 4.5.1 Culture Media

Isolated placental stem cells, or placental cell populations, or cells or placental tissue from which placental cells grow from, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GlutaMAX™ and gentamicin; DMEM comprising 10% FBS, GlutaMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Any of the culture methods and media disclosed herein can be used to culture and propagate placental stem cells as well.

4.5.2 Expansion and Proliferation of Placental Stem Cells

Once placental stem cells are isolated (e.g., separated from at least 50% of the placental cells with which the stem cell or population of stem cells is normally associated in vivo), the stem cell or population of stem cells can be proliferated and expanded in vitro. Similarly, once placental stem cells are produced, such cells can also be proliferated and expanded in vitro. For example, placental stem cells can be cultured in tissue culture containers, e.g., dishes, flasks, multiwell plates, or the like, for a sufficient time for the placental stem cells to proliferate to 70-90% confluence, that is, until the placental stem cells and their progeny occupy 70-90% of the culturing surface area of the tissue culture container.

Placental stem cells can be seeded in culture vessels at a density that allows cell growth. For example, the placental stem cells may be seeded at low density (e.g., about 1,000 to about 5,000 cells/cm$^2$) to high density (e.g., about 50,000 or more cells/cm$^2$). In a preferred embodiment, the placental stem cells are cultured at about 0 to about 5 percent by volume $CO_2$ in air. In some preferred embodiments, the placental stem cells are cultured at about 2 to about 25 percent $O_2$ in air, preferably about 5 to about 20 percent $O_2$ in air. The placental stem cells preferably are cultured at about 25° C. to about 40° C., preferably 37° C. The placental stem cells are preferably cultured in an incubator. The culture medium can be static or agitated, for example, using a bioreactor. Placental stem cells are preferably are grown under low oxidative stress (e.g., with addition of glutathione, ascorbic acid, catalase, tocopherol, N-acetylcysteine, or the like).

Once 70%-90% confluence is obtained, the placental stem cells may be passaged. For example, the cells can be enzymatically treated, e.g., trypsinized, using techniques well-known in the art, to separate them from the tissue culture surface. After removing the placental stem cells by pipetting and counting the cells, about 20,000-100,000 stem cells, preferably about 50,000 placental stem cells, are passaged to a new culture container containing fresh culture medium. Typically, the new medium is the same type of medium from which the stem cells were removed. Provided herein are populations of placental stem cells that have been passaged at least 1, 2, 3, 4, 5, 6, 7, 8, 9, 10, 12, 14, 16, 18, or 20 times, or more, and combinations of the same. In some embodiments, the population of placental stem cells has been passaged at least 3-10 times, 3-8 times, or 5-7 times.

4.6 Preservation of Placental Stem Cells

Placental stem cells useful in the treatment of ALS can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related International Patent Application Publication No. WO 2007/079185.

In one embodiment, provided herein is a method of preserving placental stem cells comprising contacting said placental stem cells with or bringing said placental stem cells into proximity to a stem cell collection composition comprising an inhibitor of apoptosis and an oxygen-carrying perfluorocarbon, wherein said inhibitor of apoptosis is present in an amount and for a time sufficient to reduce or prevent apoptosis in the population of placental stem cells, as compared to a population of placental stem cells not contacted with or brought into proximity to the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said placental stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting or bringing into proximity the stem cells. In another more specific embodiment, said apoptosis inhibitor and said perfluorocarbon are between about 2° C. and 10° C., or between about 2° C. and about 5° C., at the time of contacting or bringing into proximity the stem cells. In another more specific embodiment, said contacting or bringing into proximity is performed during transport of said placental stem cells. In another more specific embodiment, said contacting or bringing into proximity is performed during freezing and thawing of said population of stem cells.

In another embodiment, placental stem cells can be preserved by a method comprising contacting said placental stem cells with or bringing said placental stem cells into proximity to an inhibitor of apoptosis and an organ-preserving compound, wherein said inhibitor of apoptosis is present in an amount and for a time sufficient to reduce or prevent apoptosis of the placental stem cells, as compared to placental stem cells not contacted with or brought into proximity to the inhibitor of apoptosis. In a specific embodiment, the organ-preserving compound is UW solution (described in U.S. Pat. No. 4,798,824; also known as ViaSpan; see also Southard et al., *Transplantation* 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof.

In another embodiment, placental stem cells, to be used to produce placental stem cells, are contacted with or brought into proximity to a stem cell collection composition comprising an apoptosis inhibitor and oxygen-carrying perfluorocarbon, organ-preserving compound, or combination thereof, during perfusion. In another embodiment, said placental stem cells, to be used to produce placental stem cells, are contacted or brought into proximity during a process of tissue disruption, e.g., enzymatic digestion. In another embodiment, placental cells are contacted with or brought into proximity to said stem cell collection compound after collection by perfusion, or after collection by tissue disruption, e.g., enzymatic digestion.

Typically, during placental stem cell collection, enrichment and isolation, it is preferable to minimize or eliminate cell stress due to hypoxia and mechanical stress. In another embodiment of the method, therefore, placental stem cells, to be used to produce placental stem cells, are exposed to a hypoxic condition during collection, enrichment or isolation for less than six hours during said preservation, wherein a hypoxic condition is a concentration of oxygen that is less than normal blood oxygen concentration. In a more specific embodiment, said placental stem cells are exposed to said hypoxic condition for less than two hours during said preservation. In another more specific embodiment, said placental stem cells are exposed to said hypoxic condition for less than one hour, or less than thirty minutes, or is not exposed to a hypoxic condition, during collection, enrichment or isolation. In another specific embodiment, said placental stem cells are not exposed to shear stress during collection, enrichment or isolation.

The placental stem cells, as well as the placental stem cells to be used to produce placental stem cells, described herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, Plasmalyte, methylcellulose with or without glycerol. The stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

4.7 Uses of Placental Cells 4.7.1 Compositions Comprising Placental Cells

The methods of treatment provided herein can use compositions comprising the placental stem cells, or biomolecules therefrom. In the same manner, the populations of placental stem cells provided herein can be combined with any physiologically-acceptable or medically-acceptable compound, composition or device for use in, e.g., research or therapeutics.

4.7.1.1 Cryopreserved Placental Cells

The placental cells provided herein can be preserved, for example, cryopreserved for later use. Methods for cryopreservation of cells, such as stem cells, are well known in the art. Placental stem cells can be prepared in a form that is easily administrable to an individual. For example, placental stem cells described herein can be contained within a container that is suitable for medical use. Such a container can be, for example, a sterile plastic bag, flask, jar, vial, or other container from which the placental cell population can be easily dispensed. For example, the container can be a blood bag or other plastic, medically-acceptable bag suitable for the intravenous administration of a liquid to a recipient. The container is preferably one that allows for cryopreservation of the placental stem cells.

Cryopreserved placental stem cells can comprise placental stem cells derived from a single donor, or from multiple donors. The placental stem cells can be completely HLA-matched to an intended recipient, or partially or completely HLA-mismatched.

Thus, in one embodiment, provided herein is a composition comprising placental stem cells in a container. In a specific embodiment, the placental stem cells are, or have been, cryopreserved. In another specific embodiment, the container is a bag, flask, vial or jar. In a more specific embodiment, said bag is a sterile plastic bag. In a more specific embodiment, said bag is suitable for, allows for, facilitates intravenous administration of said placental stem cells. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cells are contained within a physiologically-acceptable aqueous solution. In a more specific embodiment, said physiologically-acceptable aqueous solution is a 0.9% NaCl solution. In another specific embodiment, said placental stem cells are HLA-matched to a recipient of said placental stem cells. In another specific embodiment, said placental stem cells are at least partially HLA-mismatched to a recipient of said placental stem cells. In another specific embodiment, said placental stem cells are from a plurality of donors.

4.7.1.2 Pharmaceutical Compositions

Populations of isolated placental stem cells, or populations of cells comprising the isolated placental stem cells, can be formulated into pharmaceutical compositions for use in vivo, e.g., in the methods of treatment provided herein. Such pharmaceutical compositions comprise placental stem cells, or a population of cells comprising isolated placental stem cells, in a pharmaceutically-acceptable carrier, e.g., a saline solution or other accepted physiologically-acceptable solution for in vivo administration. Pharmaceutical compositions comprising the isolated placental stem cells described herein can comprise any, or any combination, of the isolated placental stem cell populations, or isolated placental stem cells, described elsewhere herein. The pharmaceutical compositions can comprise fetal, maternal, or both fetal and maternal isolated cells. The pharmaceutical compositions provided herein can further comprise isolated placental stem cells obtained from a single individual, umbilical cord or placenta, or from a plurality of individuals, umbilical cords or placentae. Any of the placental stem cells, described elsewhere herein, can be formulated into a pharmaceutical composition, as described below.

The pharmaceutical compositions provided herein can comprise any number of isolated placental stem cells. For example, a single unit dose of isolated placental stem cells can comprise, in various embodiments, about, at least, or no more than $1\times10^5$, $3\times10^5$, $5\times10^5$, $1\times10^6$, $3\times10^6$, $5\times10^6$, $1\times10^7$, $3\times10^7$, $5\times10^7$, $1\times10^8$, $2\times10^8$, $3\times10^8$, $4\times10^8$, $5\times10^8$, $6\times10^8$, $7\times10^8$, $8\times10^8$, $8\times10^8$, $1\times10^9$, $2\times10^9$, $3\times10^9$, $4\times10^9$, $5\times10^9$, $1\times10^{10}$, $5\times10^{10}$, $1\times10^{11}$ or more isolated cells. In various embodiments, a single unit dose of isolated placental stem cells can comprise, in various embodiments, about, at least, or no more than $1\times10^4$–$5\times10^4$, $5\times10^4$–$1\times10^5$, $1\times10^5$–$5\times10^5$, $5\times10^5$–$1\times10^6$, $1\times10^6$–$5\times10^6$, $5\times10^6$–$1\times10^7$, $1\times10^7$–$5\times10^7$, $5\times10^7$–$1\times10^8$, $1\times10^8$–$5\times10^8$, $5\times10^8$–$1\times10^9$, $1\times10^9$–$5\times10^9$, $5\times10^9$–$1\times10^{10}$, $1\times10^{10}$–$5\times10^{10}$, $5\times10^{10}$–$1\times10^{11}$ or more isolated cells. In a specific embodiment, a single unit dose comprises about $1\times10^8$ placental stem cells. In a specific embodiment, a single unit dose comprises about $2\times10^8$ placental stem cells. In this context, "about" means plus or minus 5%. In certain embodiments, a single unit dose is administered all at once, or may be administered in multiple (e.g., 2, 3, 4, 5, 6, 7, 8, 9, 10, 15, 20, or more) smaller units. In certain embodiments, the multiple smaller units are administered at the same time, or within 10 minutes, 15 minutes, 30 minutes, 45 minutes, 1 hour, 2 hours, 3, hours, 4 hours, 6 hours, 8 hours, 10 hours, 12 hours, 18 hours, 24 hours, 36 hours, 48 hours, 3 days, 4 days, 5 days, 6 days, a week, 2 weeks, 3 weeks, 4 weeks, a month, or more of one another. In certain embodiments, more than one single unit dose is administered at a time, e.g., 2, 3, 4, 5, 6, 7, 8, 9, 10, 15, 20, or more times to achieve the desired administration. In certain embodiments, the more than one single unit dose (delivered at, e.g., the same time) is delivered in one infusion or injection. In certain embodiments, the more than one single unit dose (delivered at, e.g., the same time) is delivered in more than one, e.g., 2, 3, 4, 5, 5-10, 15, 10-20, 20, or 30, infusion or injection.

The pharmaceutical compositions provided herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); or stabilizers such as albumin, dextran 40, gelatin, hydroxyethyl starch, plasmalyte, and the like.

When formulated as an injectable solution, in one embodiment, the pharmaceutical composition comprises about 1% to 1.5% HSA and about 2.5% dextran. In a preferred embodiment, the pharmaceutical composition comprises from about $5 \times 10^6$ cells per milliliter to about $2 \times 10^7$ cells per milliliter in a solution comprising 5% HSA and 10% dextran, optionally comprising an immunosuppressant, e.g., cyclosporine A at, e.g., 10 mg/kg body weight.

In other embodiments, the pharmaceutical composition, e.g., a solution, comprises a plurality of cells, e.g., isolated placental stem cells, wherein said pharmaceutical composition comprises between about $1.0 \pm 0.3 \times 10^6$ cells per milliliter to about $5.0 \pm 1.5 \times 10^6$ cells per milliliter. In other embodiments, the pharmaceutical composition comprises between about $1.5 \times 10^6$ cells per milliliter to about $3.75 \times 10^6$ cells per milliliter. In other embodiments, the pharmaceutical composition comprises between about $1 \times 10^6$ cells/mL to about $50 \times 10^6$ cells/mL, about $1 \times 10^6$ cells/mL to about $40 \times 10^6$ cells/mL, about $1 \times 10^6$ cells/mL to about $30 \times 10^6$ cells/mL, about $1 \times 10^6$ cells/mL to about $20 \times 10^6$ cells/mL, about $1 \times 10^6$ cells/mL to about $15 \times 10^6$ cells/mL, or about $1 \times 10^6$ cells/mL to about $10 \times 10^6$ cells/mL. In certain embodiments, the pharmaceutical composition comprises no visible cell clumps (i.e., no macro cell clumps), or substantially no such visible clumps. As used herein, "macro cell clumps" means an aggregation of cells visible without magnification, e.g., visible to the naked eye, and generally refers to a cell aggregation larger than about 150 microns. In some embodiments, the pharmaceutical composition comprises about 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% dextran, e.g., dextran-40. In a specific embodiment, said composition comprises about 7.5% to about 9% dextran-40. In a specific embodiment, said composition comprises about 5.5% dextran-40. In certain embodiments, the pharmaceutical composition comprises from about 1% to about 15% human serum albumin (HSA). In specific embodiments, the pharmaceutical composition comprises about 1%, 2%, 3%, 4%, 5%, 6%, 7%, 8%, 9%, 10%, 11%, 12%, 13%, 14% or 15% HSA. In a specific embodiment, said cells have been cryopreserved and thawed. In another specific embodiment, said cells have been filtered through a 70 μM to 100 μM filter. In another specific embodiment, said composition comprises no visible cell clumps. In another specific embodiment, said composition comprises fewer than about 200 cell clumps per $10^6$ cells, wherein said cell clumps are visible only under a microscope, e.g., a light microscope. In another specific embodiment, said composition comprises fewer than about 150 cell clumps per $10^6$ cells, wherein said cell clumps are visible only under a microscope, e.g., a light microscope. In another specific embodiment, said composition comprises fewer than about 100 cell clumps per $10^6$ cells, wherein said cell clumps are visible only under a microscope, e.g., a light microscope.

In a specific embodiment, the pharmaceutical composition comprises about $1.0 \pm 0.3 \times 10^6$ cells per milliliter, about 5.5% dextran-40 (w/v), about 10% HSA (w/v), and about 5% DMSO (v/v).

In other embodiments, the pharmaceutical composition comprises a plurality of cells, e.g., a plurality of isolated placental stem cells in a solution comprising 10% dextran-40, wherein the pharmaceutical composition comprises between about $1.0 \pm 0.3 \times 10^6$ cells per milliliter to about $5.0 \pm 1.5 \times 10^6$ cells per milliliter, and wherein said composition comprises no cell clumps visible with the unaided eye (i.e., comprises no macro cell clumps). In some embodiments, the pharmaceutical composition comprises between about $1.5 \times 10^6$ cells per milliliter to about $3.75 \times 10^6$ cells per milliliter. In a specific embodiment, said cells have been cryopreserved and thawed. In another specific embodiment, said cells have been filtered through a 70 μM to 100 μM filter. In another specific embodiment, said composition comprises fewer than about 200 micro cell clumps (that is, cell clumps visible only with magnification) per $10^6$ cells. In another specific embodiment, the pharmaceutical composition comprises fewer than about 150 micro cell clumps per $10^6$ cells. In another specific embodiment, the pharmaceutical composition comprises fewer than about 100 micro cell clumps per $10^6$ cells. In another specific embodiment, the pharmaceutical composition comprises less than 15%, 14%, 13%, 12%, 11%, 10%, 9%, 8%, 7%, 6%, 5%, 4%, 3%, or 2% DMSO, or less than 1%, 0.9%, 0.8%, 0.7%, 0.6%, 0.5%, 0.4%, 0.3%, 0.2%, or 0.1% DMSO.

Further provided herein are compositions comprising cells, wherein said compositions are produced by one of the methods disclosed herein. For example, in one embodiment, the pharmaceutical composition comprises cells, wherein the pharmaceutical composition is produced by a method comprising filtering a solution comprising placental stem cells to form a filtered cell-containing solution; diluting the filtered cell-containing solution with a first solution to about 1 to $50 \times 10^6$, 1 to $40 \times 10^6$, 1 to $30 \times 10^6$, 1 to $20 \times 10^6$, 1 to $15 \times 10^6$, or 1 to $10 \times 10^6$ cells per milliliter, e.g., prior to cryopreservation; and diluting the resulting filtered cell-containing solution with a second solution comprising dextran, but not comprising human serum albumin (HSA) to produce said composition. In certain embodiments, said diluting is to no more than about $15 \times 10^6$ cells per milliliter. In certain embodiments, said diluting is to no more than about $10 \pm 3 \times 10^6$ cells per milliliter. In certain embodiments, said diluting is to no more than about $7.5 \times 10^6$ cells per milliliter. In other certain embodiments, if the filtered cell-containing solution, prior to the dilution, comprises less than about $15 \times 10^6$ cells per milliliter, filtration is optional. In other certain embodiments, if the filtered cell-containing solution, prior to the dilution, comprises less than about $10 \pm 3 \times 10^6$ cells per milliliter, filtration is optional. In other certain embodiments, if the filtered cell-containing solution, prior to the dilution, comprises less than about $7.5 \times 10^6$ cells per milliliter, filtration is optional.

In a specific embodiment, the cells are cryopreserved between said diluting with a first dilution solution and said diluting with said second dilution solution. In another specific embodiment, the first dilution solution comprises dextran and HSA. The dextran in the first dilution solution or second dilution solution can be dextran of any molecular weight, e.g., dextran having a molecular weight of from about 10 kDa to about 150 kDa. In some embodiments, said dextran in said first dilution solution or said second solution is about 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% dextran. In another specific embodiment, the dextran in said first dilution solution or said second dilution solution is dextran-40. In another specific embodiment, the dextran in said first dilution solution and said second dilution solution is dextran-40. In another specific embodiment, said dextran-40 in said first dilution solution is 5.0% dextran-40. In another specific embodiment, said dextran-40 in said first dilution solution is 5.5% dextran-40. In another specific embodiment, said dextran-40 in said second dilution solution is 10% dextran-40. In another specific embodiment, said HSA in said solution comprising HSA is 1 to 15% HSA. In another specific embodiment, said HSA in said solution comprising HSA is about 1%, 2%, 3%, 4%, 5%, 6%, 7%, 8%, 9%, 10%, 11%, 12%, 13%, 14% or 15% HSA. In another specific embodiment, said HSA in said solution comprising HSA is 10% HSA. In another specific embodiment, said first dilution solution comprises HSA. In a more specific embodiment, said HSA in said first dilution solution is 10% HSA. In another specific embodiment, said first dilution solution comprises a cryoprotectant. In a more specific embodiment, said cryoprotectant is DMSO. In another specific embodiment, said dextran-40 in said second dilution solution is about 10% dextran-40. In another specific embodiment, said composition comprising cells comprises about 7.5% to about 9% dextran. In another specific embodiment, the pharmaceutical composition comprises from about $1.0\pm0.3\times10^6$ cells per milliliter to about $5.0\pm1.5\times10^6$ cells per milliliter. In another specific embodiment, the pharmaceutical composition comprises from about $1.5\times10^6$ cells per milliliter to about $3.75\times10^6$ cells per milliliter.

In another embodiment, the pharmaceutical composition is made by a method comprising (a) filtering a cell-containing solution comprising placental stem cells prior to cryopreservation to produce a filtered cell-containing solution; (b) cryopreserving the cells in the filtered cell-containing solution at about 1 to $50\times10^6$, 1 to $40\times10^6$, 1 to $30\times10^6$, 1 to $20\times10^6$, 1 to $15\times10^6$, or 1 to $10\times10^6$ cells per milliliter; (c) thawing the cells; and (d) diluting the filtered cell-containing solution about 1:1 to about 1:11 (v/v) with a dextran-40 solution. In certain embodiments, if the number of cells is less than about $10\pm3\times10^6$ cells per milliliter prior to step (a), filtration is optional. In a more specific embodiment, the cells in step (b) are cryopreserved at about $10\pm3\times10^6$ cells per milliliter. In a more specific embodiment, the cells in step (b) are cryopreserved in a solution comprising about 5% to about 10% dextran-40 and HSA. In certain embodiments, said diluting in step (b) is to no more than about $15\times10^6$ cells per milliliter.

In another embodiment, the pharmaceutical composition is made by a method comprising: (a) suspending placental stem cells in a 5.5% dextran-40 solution that comprises 10% HSA to form a cell-containing solution; (b) filtering the cell-containing solution through a 70 μM filter; (c) diluting the cell-containing solution with a solution comprising 5.5% dextran-40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter; (d) cryopreserving the cells; (e) thawing the cells; and (f) diluting the cell-containing solution 1:1 to 1:11 (v/v) with 10% dextran-40. In certain embodiments, said diluting in step (c) is to no more than about $15\times10^6$ cells per milliliter. In certain embodiments, said diluting in step (c) is to no more than about $10\pm3\times10^6$ cells/mL. In certain embodiments, said diluting in step (c) is to no more than about $7.5\times10^6$ cells/mL.

In another embodiment, the composition comprising cells is made by a method comprising: (a) centrifuging a plurality of placental stem cells, to collect the cells; (b) resuspending the cells in 5.5% dextran-40; (c) centrifuging the cells to collect the cells; (d) resuspending the cells in a 5.5% dextran-40 solution that comprises 10% HSA; (e) filtering the cells through a 70 μM filter; (f) diluting the cells in 5.5% dextran-40, 10% HSA, and 5% DMSO to about 1 to $50\times10^6$, 1 to $40\times10^6$, 1 to $30\times10^6$, 1 to $20\times10^6$, 1 to $15\times10^6$, or 1 to $10\times10^6$ cells per milliliter; (g) cryopreserving the cells; (h) thawing the cells; and (i) diluting the cells 1:1 to 1:11 (v/v) with 10% dextran-40. In certain embodiments, said diluting in step (f) is to no more than about $15\times10^6$ cells per milliliter. In certain embodiments, said diluting in step (f) is to no more than about $10\pm3\times10^6$ cells/mL. In certain embodiments, said diluting in step (f) is to no more than about $7.5\times10^6$ cells/mL. In other certain embodiments, if the number of cells is less than about $10\pm3\times10^6$ cells per milliliter, filtration is optional.

The compositions, e.g., pharmaceutical compositions comprising the isolated placental cells, described herein can comprise any of the isolated placental stem cells described herein.

Other injectable formulations, suitable for the administration of cellular products, may be used.

In certain embodiments, the placental stem cells can be encapsulated in, e.g., alginate, either before or after cryopreservation. In certain embodiments, the placental stem cells can be combined with platelet-rich plasma, e.g., for local injection or local administration applications. In specific embodiments, the platelet rich plasma is autologous platelet rich plasma, e.g., autologous to the individual to whom the placental stem cells are administered. In other specific embodiments, the platelet-rich plasma is allogeneic to the individual to whom the placental stem cells are administered. In another specific embodiment, said platelet rich plasma is derived from placental perfusate. In other specific embodiments, the volume to volume ratio of placental stem cells to platelet rich plasma in the composition, or the ratio between numbers of placental stem cells and numbers of platelets, is between about 10:1 and 1:10; between about 100:1 and 1:100; or is about 1:1.

In one embodiment, the pharmaceutical composition comprises isolated placental stem cells that are substantially, or completely, non-maternal in origin, that is, have the fetal genotype; e.g., at least about 90%, 95%, 98%, 99% or about 100% are non-maternal in origin.

In a specific embodiment, the pharmaceutical composition additionally comprises stem cells that are not obtained from a placenta.

Isolated placental stem cells in the compositions, e.g., pharmaceutical compositions, provided herein, can comprise placental stem cells derived from a single donor, or from multiple donors. The isolated placental cells can be completely HLA-matched to an intended recipient, or partially or completely HLA-mismatched.

4.8 Placental Stem Cell Conditioned Media

The placental stem cells (including umbilical cord stem cells) provided herein can be used to produce conditioned medium, e.g., for the treatment of an individual having an ALS. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least 30%, 40%, 50%, 60%, 70%, 80%, 90% confluence, or up to 100% confluence. In another embodiment, the conditioned medium comprises medium in which placental stem cells and non-placental, non-umbilical cord stem cells have been cultured.

In some embodiments, provided herein is a pharmaceutical composition comprising the conditioned medium described herein. Also provided herein is a method of treating ALS comprising administering to an individual having ALS a therapeutically effective amount of conditioned medium, or conditioned medium in combination with placental stem cells or a placental cell population described herein. Such treatment methods may be used alone or in combination with a second therapeutic composition described herein.

5. EXAMPLES

5.1 Example 1: Treatment of Amyotrophic Lateral Sclerosis Using Placental Stem Cells A female patient with progressing advanced amyotrophic lateral sclerosis (ALS) was treated with CD34−, CD10+, CD105+, CD200+ placental stem cells for approximately thirteen months. For the first treatment cycle (cycle 1), about $8\times10^8$ placental stem cells were infused intravenously into the patient on Day 1 and Day 8. Beginning approximately three months after the beginning of the first cycle, $8\times10^8$ placental stem cells were infused intravenously into the patient on Day 1 and Day 8 every two months for three additional cycles (cycles 2-4). The patient tolerated the infusions of cycles 1-4 well, with minimal signs of toxicity. While the patient's overall condition was one of progressive deterioration, the patient appeared to have an acute, transient response to these infusions. The patient demonstrated improvement in performance soon after the administration of the placental stem cells. In particular, bulbar symptoms, including speech, showed clear improvement between infusion Day 1 and Day 8, which was confirmed by voice recordings. This improvement in speech was demonstrated repetitively at each cycle and was thus not an isolated finding.

Following cycle 4, there were an additional five cycles (cycles 5-9), in which infusions were given on Day 1 and Day 8 every month. For cycles 5-8, about $8\times10^8$ placental stem cells were administered per infusion, and for cycle 9, about $2\times10^8$ cells were administered per infusion. The patient tolerated the infusions of cycles 5-9 well, with minimal signs of toxicity. With the change to monthly cycles, the patient's condition stabilized, in particular, the patient's pulmonary condition stabilized. Thus, infusion of placental stem cells provides measurable benefit to a patient with progressing, advanced ALS.

5.2 Example 2: Effects of Intravenous Placental Stem Cells in ALS Mice

This example describes the use of CD34−, CD10+, CD105+, CD200+ placental stem cells to treat a mutant SOD1 transgenic mouse model of human familial ALS.

5.2.1 Study Methods

Equal numbers of male and female B6SJL-Tg(SOD1*G93A)1Gur/J mice (Jackson Laboratories, Bar Harbor, Me.) at the age 43 or 50 days old were used in the study. Animals were assigned to treatment groups based on gender, weight and rotarod performance. Animals were trained on the rotarod two to four times starting on Day 56 and then tested weekly starting on Day 63 until one of the hind limbs showed sign of paralysis. Animals were observed twice per week before 100 days of age, and daily thereafter. Data were recorded using the following scale to assess onset of disease:
1) Normal healthy animal, displayed no signs of the disease.
2) The animal failed to show the ability to fully splay its legs. This was tested by allowing the animal to grab a hold of the grating on top of the cage and then lightly pulling on the animal's tail.
3) The animal displayed tremors in one or more of its hindlimbs.
4) The animal displayed a gait abnormality. This was characterized by squatting or waddling when walking
5) The animal displayed paralysis in one or more hind limbs.

Placental stem cells that had been cryopreserved and thawed on the day of injection were used. At 100 days of age (approximate age of onset of disease), mice (50/50 male/female) were treated with one intravenous (i.v.) dose through tail vein injection as follows:
1) placental stem cells, 1.5 million cells (200 µl)
2) placental stem cells, 500,000 cells (200 µl)
3) Vehicle (freezing media, which contains all the excipients at the same concentration as the placental stem cells) (200 µl)

The approximately first half of the dose was slowly injected over 1-2 minutes, dosing was then paused for 1-2 minutes, then the remaining dose was slowly injected over 1-2 minutes. The injection site was pressed for an additional minute or two to limit back flow and bleeding.

An animal was euthanized when it could not (a) right itself within 15 seconds when placed on its side or (b) groom its face (detected by the development of infection in one or both eyes), or (c) lost >20% of its body weight. After reaching these criteria, the mice were deeply anesthetized by IP injection of ketamine (100 mg/kg) and xylazine (10 mg/kg). Upon animal euthanasia, blood, brain, and spinal cord were analyzed for signs of disease.

5.2.2 Results and Conclusion

Animals were assessed by performance on rotarod, day of disease onset, weight, and duration of survival. Independent of sex, among treated groups, the group treated with 1.5 million placental stem cells showed a strong trend toward increased animal survival from time of symptom onset compared to vehicle-treated animals. Specifically, this group of mice had a mean survival after symptom onset of 6-8 days longer than vehicle treated mice. Thus, administration of placental stem cells results in improvement in a mouse model of human ALS.

5.3 Example 3: Preclinical Study of Placental Stem Cell Effectiveness in the Treatment of ALS This Example provides additional studies that can be used to demonstrate the effectiveness of CD34−, CD10+, CD105+, CD200+ placental stem cells in the treatment of amyotrophic lateral sclerosis (ALS).

The SOD1$^{G93A}$ (superoxide dismutase mutant) mouse is an established animal model for ALS, and is available, e.g., from Jackson Laboratories (Bar Harbor, Me.) (e.g., strain B6SJL-Tg(SOD1*G93A)1Gur/J, reference number 002726). 120 adult, asymptomatic SOD1$^{G93A}$ mice of the same age are segregated into three groups; 40 mice receive between $5.0\times10^5$ and $2.5\times10^7$, preferably $1.5\times10^6$, placental stem cells; 40 mice receive between $5.0\times10^5$ and $2.5\times10^7$, preferably $1.5\times10^6$, dermal fibroblasts (e.g., from Life Technologies), and 40 mice receive vehicle only. In a variation, a cumulative dose of $4.5\times10^6$ cells (administered over 3 dosings, each dose being up to $1.5\times10^6$, and preceded with either dexamehason or heparin) is injected.

The animals are tracked for the remainder of their lifespans to assess symptoms of disease, e.g., failure to show the ability to fully splay its legs, tremors in one or more of its hindlimbs, gait abnormality, or paralysis in one or more hind limbs. The age of onset of one or more symptoms is determined (including the age in days of onset of paralysis), and the lifespan of the animals after onset of the one or more symptoms (including paralysis) is determined. Mice receiving placental stem cells are expected to have an onset of one or more symptoms (including paralysis) that is delayed, or significantly delayed, as compared to mice receiving dermal fibroblasts or vehicle. Alternatively, mice receiving placental stem cells are expected to survive longer (e.g., longer after onset of symptoms) than control mice.

After administration of cells or vehicle, mice are subjected monthly to MUNE (Motor Unit Number Estimation) analysis. Briefly, mice are anesthetized and immobilized prone, with body temperature maintained at or just above 32° C. A Teflon-insulated 0.7 mm cathode is placed close to the sciatic nerve, and a Teflon-insulated 0.7 mm anode is placed subcutaneously proximal to the cathode. Motor responses to electrical stimulation, in both flexor and extensor compartments, are recorded via a ring electrode placed circumferentially around the hindlimb. Stimuli are given from an constant current electrical source, e.g., Medtronic Keypoint (Medtronic, Minneapolis, Minn.), and recordings are made through an electromyography amplifier. Positions of the stimulating electrodes are optimized for evoking a motor response with less than 0.7 mA current, and stimulus intensity is increased until compound motor activity potentials (CMAP) are maximized. Using a repetition rate of 1/s, the stimulus intensity is increased from subthreshold levels until a small all-or-none response is evoked, after which the response is recorded after establishing its stability by three to four identical repeats. This process is repeated for a total of 10 increments. Before 10 increments are performed, a supramaximal response is obtained and used to calculate maximum CMAP area. Individual motor unit area is determined by subtracting the CMAP area of each response from that of the prior response. The average of individual values yield an estimate of average single motor unit action potential area. The area of the maximum CMAP is then divided by the preceding value to yield the MUNE. Average motor unit size is calculated by dividing maximum CMAP area by the corresponding MUNE value. It is expected that treatment of the mice with placental stem cells will result in a significantly increased motor unit number value at any given time, or a delayed rate of decline, as compared to mice receiving fibroblasts and vehicle.

Development of ALS symptoms in the mice are also analyzed weekly after administration of cells or vehicle using a rotarod. Mice are placed on a rod that is turning at, e.g., 4 revolutions per minute, and trained for three days to walk along the rod. On day 4, the first experimental day, the initial rotation rate is increased by 4 rpm every 30 seconds until 40 rpm is reached, or until the mouse falls from the rod. It is expected that mice receiving placental stem cells will show significantly increased rod walking times at any given time, or a delayed rate of decline, as compared to mice receiving dermal fibroblasts or vehicle.

5.4 Example 4: Isolation and Characterization of Placental Stem Cells

This example demonstrates the collection and isolation of adherent placental stem cells useful in the methods of treatment provided herein.

5.4.1 Isolation By Perfusion

Materials and Methods.

Placenta donors were recruited from expectant mothers that enrolled in private umbilical cord blood banking programs and provided informed consent permitting the use of the exsanguinated placenta following recovery of cord blood for research purposes. These donors permitted use of blinded data generated from the normal processing of their umbilical cord blood specimens for cryopreservation. This allowed comparison between the composition of the collected cord blood and the effluent perfusate recovered using this experimental method described below.

Following exsanguination of the umbilical cord and placenta, the placenta was placed in a sterile, insulated container at room temperature and delivered to the laboratory within 4 hours of birth. Placentas were discarded if, on inspection, they had evidence of physical damage such as fragmentation of the organ or avulsion of umbilical vessels. Placentas were maintained at room temperature (23+/−2° C.) or refrigerated (4° C.) in sterile containers for 2 to 20 hours. Periodically, the placentas were immersed and washed in sterile saline at 25+/−3° C. to remove any visible surface blood or debris. The umbilical cord was transected approximately 5 cm from its insertion into the placenta and the umbilical vessels were cannulated with Teflon or polypropylene catheters connected to a sterile fluid path allowing bidirectional perfusion of the placenta and recovery of the effluent fluid. The system employed herein enabled all aspects of conditioning, perfusion and effluent collection to be performed under controlled ambient atmospheric conditions as well as real-time monitoring of intravascular pressure and flow rates, core and perfusate temperatures and recovered effluent volumes. A range of conditioning protocols was evaluated over a 24 hour postpartum period and the cellular composition of the effluent fluid was analyzed by flow cytometry, light microscopy and colony forming unit assays.

Placental Conditioning.

A placenta was maintained under varying conditions in an attempt to simulate and sustain a physiologically compatible environment for the proliferation and recruitment of placental stem cells. A cannula was flushed with IMDM serum-free medium (GibcoBRL, NY) containing 2 U/ml heparin (EJkins-Sinn, N.J.). Perfusion of the placenta was performed at a rate of 50 mL per minute until approximately 150 mL of perfusate was collected. This volume of perfusate was labeled the "early fraction". The placenta was perfused at the same rate to collect a second fraction of approximately 150 mL, which was labeled the "late fraction". During the course of the procedure, the placenta was gently massaged to aid in the perfusion process and assist in the recovery of cellular material. Effluent fluid was collected from the perfusion circuit by both gravity drainage and aspiration through the arterial cannula.

Placentas were obtained from delivery rooms along with cord blood after obtaining written parental consent, and were processed at room temperature within 12 to 24 hours after delivery. Before processing, the membranes were removed and the maternal site washed clean of residual blood. The umbilical vessels were cannulated with catheters made from 20 gauge Butterfly needles use for blood sample collection. Placentas were then perfused with heparinized (2 U/mL) Dulbecco's modified Eagle Medium (HDMEM) at the rate of 15 mL/minute for 10 minutes and the perfusates were collected from the maternal sites within one hour and the nucleated cells counted. The perfusion and collection procedures were repeated once or twice until the number of recovered nucleated cells fell below 100/µL. The perfusates were pooled and subjected to light centrifugation to remove platelets, debris and de-nucleated cell membranes. The nucleated cells were then isolated by Ficoll-Hypaque density gradient centrifugation and after washing, resuspended in HDMEM. For isolation of adherent cells, aliquots of 5-10× $10^6$ cells were placed in each of several T-75 flasks and cultured with commercially available Mesenchymal Stem Cell Growth Medium (MSCGM) obtained from BioWhittaker, and placed in a tissue culture incubator at 37° C., 5% $CO_2$. After 10 to 15 days, the non-adherent cells were removed by washing with PBS, which was then replaced by MSCGM. The flasks were examined daily for the presence of various adherent cell types and in particular, for identification and expansion of clusters of fibroblastoid cells.

Cell Recovery and Isolation.

Cells were recovered from the perfusates by centrifugation at about 200×g for 15 minutes at room temperature. This procedure served to separate cells from contaminating debris and platelets. The cell pellets were resuspended in IMDM serum-free medium containing 2 U/ml heparin and 2 mM EDTA (GibcoBRL, NY). The total mononuclear cell fraction was isolated using Lymphoprep (Nycomed Pharma, Oslo, Norway) according to the manufacturer's recommended procedure and the mononuclear cell fraction was resuspended. Cells were counted using a hemocytometer. Viability was evaluated by trypan blue exclusion. Isolation of mesenchymal cells was achieved by differential trypsinization using a solution of 0.05% trypsin with 0.2% EDTA (Sigma). Differential trypsinization was possible because fibroblastoid cells detached from plastic surfaces within about five minutes whereas the other adherent populations required more than 20-30 minutes incubation. The detached fibroblastoid cells were harvested following trypsinization and trypsin neutralization using Trypsin Neutralyzing Solution (TNS, BioWhittaker). The cells were washed in HDMEM and resuspended in MSCGM. Flow cytometry of the cells was carried out using a Becton-Dickinson FACSCalibur instrument using FITC and PE labeled monoclonal antibodies selected on the basis of known markers for bone marrow-derived MSC (mesenchymal stem cells). Antibodies were purchased from B.D. and Caltag laboratories (South San Francisco, Calif.), and SH2, SH3 and SH4 antibody producing hybridomas were obtained from ATCC and reactivities of the antibodies in their cultured supernatants were detected by FITC or PE labeled F(ab)'$_2$ goat anti-mouse antibodies. Lineage differentiation was carried out using the commercially available induction and maintenance culture media (BioWhittaker), used as per manufacturer's instructions.

Isolation of Placental Stem Cells.

Microscopic examination of the adherent cells in the culture flasks revealed morphologically different cell types, including spindle-shaped cells, round cells with large nuclei and numerous perinuclear small vacuoles, and star-shaped cells with several projections, through one of which the cells were attached to the flask. No attempts were made to further characterize these types of adherent cells, because similar non-stem cells were observed in the culture of bone marrow, cord and peripheral blood. However, fibroblastoid cells, appearing last as clusters and appearing by visual inspection to be similar to bone marrow-derived mesenchymal stem cells, were isolated by differential trypsinization and subcultured in secondary flasks. Phase microscopy of the cells, which appeared rounded after trypsinization, showed them to be highly granulated, and similar to bone marrow-derived MSC produced in the laboratory or purchased from BioWhittaker.

When subcultured, these adherent placental cells, in contrast to their earlier phase, adhered within hours, assumed characteristic fibroblastoid shape, and formed a growth pattern similar to the reference bone marrow-derived MSC. Moreover, during subculturing and refeeding, the loosely bound mononuclear cells were washed out and the cultures remained homogeneous and devoid of any visible non-fibroblastoid cell contaminants.

In subsequent experiments, the cell surface marker phenotype, or, in the case of OCT-4, the gene expression phenotype, of these adherent cells, obtained from different perfusion experiments, was characterized. The results of these experiments are shown in Table 1, below:

TABLE 1

Characterization of placental stem cells collected from separate perfusion experiments.

| PLACENTA | CD34 | CD45 | CD10 | CD29 | CD54 | SH2 | SH3 | SH4 | SSEA4 | CD44 | HLA1 | CD90 | Oct4 |
|---|---|---|---|---|---|---|---|---|---|---|---|---|---|
| 1 | − | − | + | + | + | + | + | + | | | | | |
| 2 | − | − | + | + | + | + | + | + | | | | | |
| 3 | − | − | + | + | + | + | + | + | | | | | + |
| 4 | − | − | + | + | + | + | + | + | | | | | |
| 5 | − | − | +/low | + | + | + | + | + | | | | | + |
| 6 | − | − | + | + | + | + | + | + | | | | | + |
| 7 | − | − | + | + | + | + | + | + | | | | | + |
| 8 | − | − | + | + | + | + | + | + | | | | | + |
| 9 | − | − | + | + | + | + | + | + | | | | | + |
| 10 | − | − | + | + | + | + | + | + | | + | + | + | |
| 11 | − | − | + | + | + | + | + | + | | + | + | + | |
| 12 | − | − | + | + | + | + | + | + | | + | + | + | |
| 13 | − | − | + | + | + | + | + | + | | + | + | + | |
| 14 | − | − | + | + | + | + | + | + | | + | + | + | |
| 15 | − | − | + | + | + | + | + | + | | + | + | + | |
| 16 | − | − | + | + | + | + | + | + | +/− | + | + | + | |
| 17 | − | − | + | + | + | + | + | + | | + | + | + | |
| 18 | − | − | + | + | + | + | + | + | | + | + | + | |
| 19 | − | − | + | + | + | + | + | + | | + | + | + | |

+: Detected by flow cytometry, or, for OCT-4, gene expression detected by RT-PCR
−: Not detected
Blank: Presence of marker was not tested 5.4.2 Isolation of Placental Stem Cells by Perfusion or Enzymatic Digestion and Subsequent Culture Placental stem cells are obtained from a post-partum mammalian placenta either by perfusion or by physical disruption, e.g., enzymatic digestion. The cells are cultured in a culture medium comprising 60% DMEM-LG (Gibco), 40% MCDB-201 (Sigma), 2% fetal calf serum (FCS) (Hyclone Laboratories), 1× insulin-transferrin-selenium (ITS), 1× linoleic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

The culture flask in which the cells are cultured is prepared as follows. T75 flasks are coated with fibronectin (FN), by adding 5 ml PBS containing 5 ng/ml human FN (Sigma F0895) to the flask. The flasks with FN solution are left at 37° C. for 30 min. The FN solution is then removed prior to cell culture. There is no need to dry the flasks following treatment. Alternatively, the flasks are left in contact with the FN solution at 4° C. overnight or longer; prior to culture, the flasks are warmed and the FN solution is removed.

5.4.2.1 Placental Stem Cells Isolated by Perfusion

Cultures of placental stem cells from placental perfusate are established as follows. Cells from a Ficoll gradient are seeded in FN-coated T75 flasks, prepared as above, at $50$-$100 \times 10^6$ cells/flask in 15 ml culture medium. Typically, 5 to 10 flasks are seeded. The flasks are incubated at 37° C. for 12-18 hrs to allow the attachment of adherent cells. 10 ml of warm PBS is added to each flask to remove cells in suspension, and mixed gently. 15 mL of the medium is then removed and replaced with 15 ml fresh culture medium. All medium is changed 3-4 days after the start of culture. Subsequent culture medium changes are performed, during which 50% or 7.5 ml of the medium is removed.

Starting at about day 12, the culture is checked under a microscope to examine the growth of the adherent cell colonies. When cell cultures become approximately 80% confluent, typically between day 13 to day 18 after the start of culture, adherent cells are harvested by trypsin digestion. Cells harvested from these primary cultures are designated passage 0 (zero).

5.4.2.2 Placental Stem Cells Isolated by Physical Disruption and Enzymatic Digestion Placental stem cell cultures are established from digested placental tissue as follows. The perfused placenta is placed on a sterile paper sheet with the maternal side up. Approximately 0.5 cm of the surface layer on maternal side of placenta is scraped off with a blade, and the blade is used to remove a placental tissue block measuring approximately $1 \times 2 \times 1$ cm. This placenta tissue is then minced into approximately 1 mm$^3$ pieces. These pieces are collected into a 50 ml Falcon tube and digested with collagenase IA (2 mg/ml, Sigma) for 30 minutes, followed by trypsin-EDTA (0.25%, GIBCO BRL) for 10 minutes, at 37° C. in water bath. The resulting solution is centrifuged at 400 g for 10 minutes at room temperature, and the digestion solution is removed. The pellet is resuspended to approximately 10 volumes with PBS (for example, a 5 ml pellet is resuspended with 45 ml PBS), and the tubes are centrifuged at 400 g for 10 minutes at room temperature. The tissue/cell pellet is resuspended in 130 mL culture medium, and the cells are seeded at 13 ml per fibronectin-coated T-75 flask. Cells are incubated at 37° C. with a humidified atmosphere with 5% $CO_2$. Placental Stem Cells are optionally cryopreserved at this stage.

Subculturing and Expansion of Placental Stem Cells

Cryopreserved cells can be quickly thawed in a 37° C. water bath. Placental stem cells are immediately removed from the cryovial with 10 ml warm medium and transferred to a 15 ml sterile tube. The cells are centrifuged at 400 g for 10 minutes at room temperature. The cells are gently resuspended in 10 ml of warm culture medium by pipetting, and viable cell counts are determined by Trypan blue exclusion. Cells are then seeded at about 6000-7000 cells per cm$^2$ onto FN-coated flasks, prepared as above (approximately $5 \times 10^5$ cells per T-75 flask). The cells are incubated at 37° C., 5% $CO_2$ and 90% humidity. When the cells reached 75-85% confluency, all of the spent media is aseptically removed from the flasks and discarded. 3 ml of 0.25% trypsin/EDTA (w/v) solution is added to cover the cell layer, and the cells are incubated at 37° C., 5% $CO_2$ and 90% humidity for 5 minutes. The flask is tapped once or twice to expedite cell detachment. Once >95% of the cells are rounded and detached, 7 ml of warm culture medium is added to each T-75 flask, and the solution is dispersed by pipetting over the cell layer surface several times.

After counting the cells and determining viability as above, the cells are centrifuged at 1000 RPM for 5 minutes at room temperature. Cells are passaged by gently resuspending the cell pellet from one T-75 flask with culture medium, and evenly plating the cells onto two FN-coated T-75 flasks.

5.4.3 Cellular Marker Profile of Placental Stem Cells

This Example demonstrates an exemplary cellular marker profile of placental stem cells.

Placental stem cells or umbilical cord stem cells, were obtained by enzymatic digestion as described above. Cells in culture medium were washed once by adding 2 mL 2% FBS-PBS and centrifuging at 400 g for 5 minutes. The supernatant was decanted, and the pellet was resuspended in 100-200 μL 2% FBS-PBS. 4 tubes were prepared with BD™ CompBeads (Cat#552843) by adding 100 μl of 2% FBS-PBS to each tube, adding 1 full drop (approximately 60 IA) of the BD™ CompBeads Negative Control and 1 drop of the BD™ CompBeads Anti-Mouse beads to each tube, and vortexing. To the 4 tubes of BD™ CompBeads, the following antibodies were added:

TABLE 2

| Tube# | Antibody | Cat# | Clone | Volume μL |
|---|---|---|---|---|
| 1 | CD105 FITC | FAB10971F | 166707 | 10 |
| 2 | CD200 PE | 552475 | MRC-OX-104 | 20 |
| 3 | CD10 PE-Cy7 | 341102 | HI10a | 5 |
| 4 | CD34 APC | 340667 | 8G12 | 5 |

Control tubes were prepared as follows:

TABLE 3

| Tube# | Antibody | Cat# | Clone | Volume μL |
|---|---|---|---|---|
| 1 | Unstained | — | — | — |
| 2 | IgG FITC/IgG PE// IgG APC | 555787, 555786, 550931 | G18-145 | 10 ea |

The following antibodies were added to the sample tubes:

TABLE 4

| Antibody | Cat# | Clone | Volume μL |
|---|---|---|---|
| CD105 FITC | FAB10971F | 166707 | 10 |
| CD200 PE | 552475 | MRC-OX-104 | 20 |
| CD10 PE-Cy7 | 341102 | HI10a | 5 |
| CD34 APC | 340667 | 8G12 | 5 |

The control and sample tubes were incubated in the dark at room temperature for 30 minutes. After incubation, the tubes were washed by adding 2 mL 2% FBS-PBS and centrifuging at 400 g for 5 minutes. The supernatant was decanted, and the pellet was resuspended in 100-200 μL, 2%

FBS-PBS and acquire on flow cytometer. All other antibodies were used following this procedure.

Matched placental stem cells from amniotic membrane and umbilical cord stem cells were analyzed using fluorescently-labeled antibodies and flow cytometry to identify cell surface markers that were present or absent. Markers analyzed included CD105 (proliferation related endothelial specific marker); CD200 (marker associated with regulatory function); CD34 (expressed on endothelial cells and on hematopoietic stem cells); CD10 (stem cell/precursor cell marker); cytokeratin K (epithelial marker); CD44 (cell migration, lymphocyte homing, hematopoeisis); CD45 (lineage marker); CD133 (marker for hematopoietic progenitor cells); CD117 (stem cell factor (c-Kit)); CD90 (expressed on primitive hematopoietic stem cells in normal bone marrow, cord blood and fetal liver cells); HLA ABC (pan MHC I, antigen presentation, immunogenicity); β-2-microglobulin (associates with MHC I, antigen presentation, immunogenicity); HLA DR,DQ,DP (pan MHC II, antigen presentation, immunogenicity); and CD80/86 (co-stimulatory molecules for antigen presentation).

Flow cytometry results showed that for the placental stem cells that were tested, 93.83% of cells were CD105$^+$ 90.76% of cells were CD200$^+$, and 86.93% of cells were both CD105$^+$ and CD200$^+$. 99.97% of cells were CD10$^+$ 99.15% of cells were CD34$^-$, and 99.13% of cells were both CD10$^+$ and CD34$^-$. 98.71% of cells were cytokeratin positive, 99.95% of cells were CD44$^+$, and 98.71% of cells were positive for both cytokeratin and CD44. 99.51% of cells were CD45$^-$, 99.78% of cells were negative for CD133, and 99.39% of cells were negative for both CD45 and CD133. 99.31% of cells were positive for CD90, 99.7% were negative for CD117, and 99.01% were positive for CD90 and negative for CD117. 95.7% of cells were negative for both CD80 and CD86.

Flow cytometry results for umbilical cord stem cells showed that 95.95% of cells were CD200$^+$, 94.71% were CD105$^+$ and 92.69% were CD105$^+$ and CD200$^'$. 99.93% of the cells were CD10$^+$ 99.99% of the cells were CD34$^-$, and 99.6% of the cells were both CD10$^+$ and CD34$^-$. 99.45% of the cells were cytokeratin positive, 99.78% of the cells were CD44$^+$, and 99.3% of the cells were positive for both cytokeratin and CD44. 99.33% of the cells were CD45$^-$, 99.74% were CD133$^-$, and 99.15% of the cells were both CD45$^-$ and CD133$^-$. 99.84% of the cells were CD117$^-$, 98.78% of the cells were CD90$^+$, and 98.64% of the cells were both CD90$^+$ and CD117$^-$.

The phenotype CD200$^+$, CD105$^+$, CD10$^+$, CD34$^-$ appeared to be consistent over numerous such analyses. This phenotype is additionally positive for CD90, CD44, HLA ABC, β-2-microglobulin, and cytokeratin K, and negative for HLA DR,DQ,DP, CD117, CD133, and CD45.

Subsequent characterization experiments additionally determined that the placental stem cells were positive for expression of Programmed Death-1 Ligand (PDL1) and CD106/VCAM, and negative for expression of alpha smooth muscle actin (αSMA), CD38, CD133, KDR (VEGFR2), CD62E, CD62L, 144/VE-cadherin, and CD184/CXCR4.

5.4.4 Differential Gene Expression by Placental Stem Cells

Gene expression patterns from placental stem cells from amnion-chorion (AC) and umbilical cord (UC), which were predominantly CD34$^-$, CD10$^+$, CD105$^+$ and CD200$^+$, were compared to gene expression patterns of multipotent bone marrow-derived mesenchymal stem cells (BM) and dermal fibroblasts (DF), the latter of which are considered to be terminally differentiated. A set of genes was identified that are up-regulated in AC and UC, and either down-regulated or absent in BM and DF, and that are expressed independent of passage number. This set of placental stem cell- or umbilical cord stem cell-specific genes encodes a number of cytoskeleton and cell-to-cell adhesion proteins associated with epithelial cells and an immunoglobulin-like surface protein, CD200, implicated in maternal-fetal immune tolerance. Placental stem cells and umbilical cord stem cells are referred to collectively hereinafter in this Example as AC/UC stem cells.

5.4.4.1 Cells and Cell Culture

BM (Cat# PT-2501) and DF (Cat# CC-2511) were purchased from Cambrex. AC and UC originated from passage 0 tissue culture flasks. AC and UC in the flasks were obtained by digestion from a donor placenta designated 2063919. T-75 culture flasks were seeded at 6000 cells/cm$^2$ and cells were passaged when they became confluent. Population doublings were estimated from trypan blue cell counts. Cultures were assayed for gene expression after 3, 11-14, and 24-38 population doublings.

5.4.4.2 RNA, Microarrays, and Analysis

Cells were lysed directly in their tissue culture flasks, with the exception of one culture that was trypsinized prior to lysis. Total RNA was isolated with the RNeasy kit from QIAGEN. RNA integrity and concentrations were determined with an Agilent 2100 Bioanalyzer. Ten micrograms of total RNA from each culture were hybridized on an Affymetrix GENECHIP® platform. Total RNA was converted to labeled cRNAs and hybridized to oligonucleotide Human Genome U133A 2.0 arrays according to the manufacture's methods. Image files were processed with the Affymetrix MAS 5.0 software, and normalized and analyzed with Agilent GeneSpring 7.3 software.

5.4.4.3 Selection of BM-MSC, AC/UC Stem Cell, and DF Culture Time-Points for Microarray Analyses To establish a gene expression pattern unique to AC/UC stem cells, two stem cell lines, AC(6) and UC(6), were cultured in parallel with BM-MSC and DF. To maximize identifying a gene expression profile attributable to cellular origin and minimize exogenous influences all cells were grown in the same medium, seeded, and sub-cultured using the same criteria. Cells were harvested after 3 population doublings, 11-14 doublings, or 35 doublings or senescence, whichever came first. Genes whose expression in AC/UC stem cells are unchanged by time-in-culture and are up-regulated relative to BM and DF are candidates for AC/UC stem cell-specific genes.

In total twelve samples were collected. BM, AC(6), and UC(6) were harvested after three population doublings; these samples were regarded as being in culture for a "short" period of time. A short-term DF sample was not collected. Intermediate length cultures, 11 to 14 doublings, were collected for all cell types. Long-term cultures were collected from all cell lines at about 35 population doublings or just prior to senescence, whichever came first. Senescence occurred before 15 doublings for BM and at 25 doublings for DF. The purchased BM and DF cells were expanded many times prior to gene analysis, and cannot be considered early-stage. However, operationally, BM grown for three doublings (BM-03) are deemed a short-term culture. Likewise, BM-11 is operationally referred to as an intermediate length culture, but because senescence occurred at 14 doublings, BM-11 is most likely a long-term culture biologically.

5.4.4.4 Hierarchical Clustering Shows Relatedness Between BM, AC/UC Stem Cells, and DF Microarray analysis identifies patterns of gene expression, and hierarchical clustering (HC) attempts to find similarities in the context of two dimensions—genes in the first dimension and different conditions (different RNA samples) in the second. The GeneChips used in this experiment contained over 22,000 probe sets (referred to as the "all genes list"), but many of these sets interrogate genes that are not expressed in any condition. To reduce the all genes list, genes not expressed or expressed at low levels (raw values below 250) in all samples were eliminated to yield a list of 8,215 genes.

5.4.4.5 Gene Expression Analysis Using the Line Graph View

Gene expression patterns of the 8,215 genes were displayed using the line graph view in GeneSpring (data not shown). The x-axis shows the twelve experimental conditions and the y-axis shows the normalized probe set expression values on a log scale. The y-axis covers a 10,000-fold range, and genes that are not expressed or expressed at very low levels are set to a value of 0.01. By default the normalized value is set to 1. Each line represents a single gene and runs across all twelve conditions as a single color. Colors depict relative expression levels, as described for the heatmaps, but the coloring pattern is determined by selecting one condition. Genes up-regulated relative to the normalized value are displayed by the software as red, and those that are down-regulated, are displayed as blue. The obvious upward and downward pointing spikes in AC-03 through UC-11 indicate that many genes are differentially expressed across these conditions. The striking similarity in the color patterns between AC-03 and UC-03 show that many of the same genes are up or down-regulated in these two samples. Horizontal line segments indicate that a gene's expression level is unchanged across a number of conditions. This is most notable by comparing UC-36, UC-38, and UC-38-T (trypsinized). There are no obvious spikes, but there is a subtle trend in that a number of red lines between UC-36 and UC-38-T are below the normalized value of 1. This indicates that these genes, which are up-regulated in AC-03 and UC-03, are down-regulated in the later cultures. The fact that the expression patterns between UC-38 and UC-38-T are so similar indicates that trypsinizing cells just prior to RNA isolation has little effect on gene expression.

In addition to the computationally intensive HC method, by visual inspection the two BM samples are more similar to each other than to the other conditions. The same is true for the two DF cultures. And despite the large number of differentially expressed genes present in the BM and DF samples, the general appearance suggests that two BMs and the two DFs are more similar to each other than to AC/UC stem cells. This is confirmed by the HC results described above.

When the above process is applied using AC-11 as the selected condition, it is clear that AC-11 and UC-11 share many of the same differentially expressed genes, but the total number of genes in common between these two conditions appears less than the number of differentially expressed genes shared by AC-03 and UC-03. The majority of genes up-regulated in AC-03 are also up-regulated in UC-03, and more divergent in BM and DF.

5.4.4.6 Filtering Methods Used to Identify AC/UC Stem Cell-Specific Genes

Genes that remain constant across all AC/UC samples, and are down-regulated in BM and DF, are considered AC/UC stem cell-specific. Two filtering methods were combined to create a list of 58 AC/UC stem cell-specific genes (Table 5).

TABLE 5

| 58 Placental stem cell or Umbilical cord stem cell-specific genes | | |
|---|---|---|
| Symbol | Gene | Biological Process, Description, and Additional Annotation |
| ACTG2 | actin, gamma 2, smooth muscle, enteric | muscle development, cytoskeleton, expressed in umbilical cord artery and prostate epithelia |
| ADARB1 | adenosine deaminase, RNA-specific, B1 (RED1 homolog rat) | RNA processing, central nervous system development |
| AMIGO2 | amphoterin induced gene 2 | homophilic and heterophilic cell adhesion, adhesion molecule with Ig like domain 2 |
| ARTS-1 | type 1 tumor necrosis factor receptor shedding aminopeptidase regulator | proteolysis, antigen processing, angiogenesis, expressed in placenta |
| B4GALT6 | UDP-Gal:betaGlcNAc beta 1,4-galactosyltransferase, polypeptide 6 | carbohydrate metabolism, integral to membrane, may function in intercellular recognition and/or adhesion |
| BCHE | Butyrylcholinesterase | cholinesterase activity, serine esterase activity, hydrolase activity |
| C11orf9 | chromosome 11 open reading frame 9 | hypothetical protein, p53-like transcription factor, expressed in retinal pigment epithelium |
| CD200 | CD200 antigen | immunoglobulin-like, surface protein, inhibits macrophage |
| COL4A1 | collagen, type IV, alpha 1 | ECM, basement membrane, afibrillar collagen, contains arresten domain |
| COL4A2 | collagen, type IV, alpha 2 | ECM, biogenesis, basement membrane, coexpressed with COL 4A1, down-reg. in dysplastic epithelia |
| CPA4 | carboxypeptidase A4 | proteolytic, histone acetylation, maternal imprinted, high expression in prostate cancer cell lines |

TABLE 5-continued

58 Placental stem cell or Umbilical cord stem cell-specific genes

| Symbol | Gene | Biological Process, Description, and Additional Annotation |
|---|---|---|
| DMD | dystrophin (muscular dystrophy, Duchenne and Becker types) | muscle contraction, cell shape and cell size control, muscle development |
| DSC3 | desmocollin 3 | homophilic cell-cell adhesion, localized to desmosomes |
| DSG2 | desmoglein 2 | homophilic cell-cell adhesion, localized to desmosomes |
| ELOVL2 | elongation of very long chain fatty acids (FEN1/Elo2, SUR4/Elo3, yeast)-like 2 | fatty acid biosynthesis, lipid biosynthesis |
| F2RL1 | coagulation factor II (thrombin) receptor-like 1 | G-protein coupled receptor protein signaling pathway, highly expressed in colon epithelia and neuronal elements |
| FLJ10781 | hypothetical protein FLJ10781 | — |
| GATA6 | GATA binding protein 6 | transcription factor, muscle development |
| GPR126 | G protein-coupled receptor 126 | signal transduction, neuropeptide signaling pathway |
| GPRC5B | G protein-coupled receptor, family C, group 5, member B | G-protein coupled receptor protein signaling pathway, |
| ICAM1 | intercellular adhesion molecule 1 (CD54), human rhinovirus receptor | cell-cell adhesion, cell adhesion, transmembrane receptor activity, expressed in conjunctival epithelium |
| IER3 | immediate early response 3 | anti-apoptosis, embryogenesis and morphogenesis, cell growth and/or maintenance |
| IGFBP7 | insulin-like growth factor binding protein 7 | negative regulation of cell proliferation, overexpressed in senescent epithelial cells |
| IL1A | interleukin 1, alpha | immune response, signal transduction, cytokine activity, cell proliferation, differentiation, apoptosis |
| IL1B | interleukin 1, beta | immune response, signal transduction, cytokine activity, cell proliferation, differentiation, apoptosis |
| 1L6 | interleukin 6 (interferon, beta 2) | cell surface receptor linked signal transduction, immune response |
| KRT18 | keratin 18 | morphogenesis, intermediate filament, expressed in placenta, fetal, and epithelial tissues |
| KRT8 | keratin 8 | cytoskeleton organization and biogenesis, phosphorylation, intermediate filament, coexpressed with KRTIB |
| LIPG | lipase, endothelial | lipid metabolism, lipoprotein lipase activity, lipid transporter, phospholipase activity, involved in vascular biology |
| LRAP | leukocyte-derived arginine aminopeptidase | antigen processing, endogenous antigen via MHC class I; N-terminal aminopeptidase activity |
| MATN2 | matrilin 2 | widely expressed in cell lines of fibroblastic or epithelial origin, nonarticular cartilage ECM |
| MEST | mesoderm specific transcript homolog (mouse) | paternally imprinted gene, development of mesodermal tissues, expressed in fetal tissues and fibroblasts |
| NFE2L3 | nuclear factor (erythroid-derived 2)-like 3 | transcription co-factor, highly expressed in primary placental cytotrophoblasts but not in placental fibroblasts |
| NUAK1 | NUAK family, SNF1-like kinase, I | protein amino acid phosphorylation, protein serine-threonine kinase activity |
| PCDH7 | BH-protocadherin (brain-heart) | cell-cell adhesion and recognition, containing 7 cadherin repeats |
| PDLIM3 | PDZ and LIM domain 3 | alpha-actinin-2-associated LIM protein, cytoskeleton protein binding, expressed in skeletal muscle |
| PKP2 | plakophilin 2 | cell-cell adhesion, localized to desmosomes, found in epithelia, binds cadherins and intermediate filament |
| RTN1 | reticulon 1 | signal transduction; neuron differentiation, neuroendocrine secretion, membrane trafficking in neuroendocrine cells |
| SERPINB9 | serpin peptidase inhibitor, clade B (ovalbumin), member 9 | serine protease inhibitor, coagulation, fibrinolysis, complement fixation, matrix remodeling, expressed in placenta |
| ST3GAL6 | sialyltransferase 10 | amino sugar metabolism, protein amino acid glycosylation, glycolipid metabolism, protein-lipoylation |

TABLE 5-continued

58 Placental stem cell or Umbilical cord stem cell-specific genes

| Symbol | Gene | Biological Process, Description, and Additional Annotation |
|---|---|---|
| ST6GALNAC5 | sialyltransferase 7E | protein amino acid glycosylation, ganglioside biosynthesis |
| SLC12A8 | solute carrier family 12 (sodium/potassium/chloride transporters), member 8 | amino acid-polyamine transporter activity, cation-chloride cotransporter 9, possible role in epithelial immunity (psoriasis) |
| TCF21 | transcription factor 21 | regulation of transcription, mesoderm development, found in epithelial cells of the kidney |
| TGFB2 | transforming growth factor, beta 2 | regulation of cell cycle, signal transduction, cell-cell signaling, cell proliferation, cell growth |
| VTN | vitronectin (serum spreading factor, somatomedin B, complement S-protein) | immune response, cell adhesion, secreted protein, binds ECM |
| ZC3H12A | zinc finger CCCM-type containing 12A | MCP-I treatment-induced protein, nucleic acid binding, hypothetical zinc finger protein |

First, 58 genes were identified by selecting those genes over-expressed three-fold in at least seven of eight AC/UC stem cell conditions relative to all BM and DF samples. Filtering on eight of the eight AC/UC stem cell conditions yielded a similar list. The second filtering method used "absent" and "present" calls provided by the Affymetrix MAS 5.0 software. A list was created by identifying genes absent in all BM and DF conditions and present in AC-03, AC-11, UC-03, and UC-11. Gene calls in the later AC/UC stem cell conditions were not stipulated.

The two lists overlapped significantly and were combined. The combined list was trimmed further by eliminating (1) several genes expressed at very low levels in most or all AC/UC stem cell conditions, and (2) genes carried on the Y chromosome. AC and UC cells used in this study were confirmed to be male by FISH analysis, and the BM and DF were derived from a female donor. The resulting list of 46 AC/UC stem cell-specific genes is shown in Table 6.

TABLE 6

AC/UC-Specific Genes Listed by Ontology

| Cell Adhesion | Cytoskeletal | Development | ECM | Implicated in |
|---|---|---|---|---|
| AMIGO2 | ACTG2 | ADARB1 | COL4A1 | Epithelia |
| B4GALT6 | DMD | IER3 | COL4A2 | ACTG2 |
| DSC3 | KRT18 | IGFBP7 | MATN2 | C11orf9 |
| DSG2 | KRT8 | IL1A | VTN | COL4A1 |
| ICAM1 | PDLIM3 | IL1B | | COL4A2 |
| PCDH7 | | MEST | | DSC3 |
| PKP2 | | TGFB2 | | DSG2 |
| VTN | | | | F2RL1 |
| Glycosylation | Response | Proteolysis | Signaling | ICAM1 |
| B4GALT6 | Immune | ARTS-1 | F2RL1 | IGFBP7 |
| ST3GAL6 | ARTS-1 | CPA4 | GPR126 | IL6 |
| ST6GALNAC5 | CD200 | LRAP | GPRC5B | KRT18 |
| Transcription | IL1A | | IL1A | KRT8 |
| C11orf9? | IL1B | | IL1B | MATN2 |
| GATA6 | IL6 | | IL6 | PKP2 |
| NFE2L3 | LRAP | | RTN1 | SLC12A8 |
| TCF21 | SLC12A8 | | TGFB2 | TCF21 |
| | VTN | | | |

This list of 46 genes encodes a collection of proteins presenting a number of ontology groups. The most highly represented group, cell adhesion, contains eight genes. No genes encode proteins involved in DNA replication or cell division. Sixteen genes with specific references to epithelia are also listed.

5.4.4.7 Discussion

An expression pattern specific to placental stem cells, and distinguishable from bone marrow-derived mesenchymal cells, was identified. Operationally, this pattern includes 46 genes that are over expressed in all placental stem cell samples relative to all BM and DF samples.

The experimental design compared cells cultured for short, medium, and long periods of time in culture. For AC and UC cells, each culture period has a characteristic set of differentially expressed genes. During the short-term or early phase (AC-03 and UC-03) two hundred up-regulated genes regress to the mean after eight population doublings. Without being bound by theory, it is likely that this early stage gene expression pattern resembles the expression profile of AC and UC while in the natural placental environment. In the placenta these cells are not actively dividing, they are metabolizing nutrients, signaling between themselves, and securing their location by remodeling the extracellular surroundings.

Gene expression by the intermediate length cultures is defined by rapid cell division and genes differentially expressed at this time are quite different from those differentially expressed during the early phase. Many of the genes up-regulated in AC-11 and UC-11, along with BM-03 and DF-14, are involved in chromosome replication and cell division. Based on gene expression, BM-03 appears biologically to be a mid-term culture. In this middle stage cell type-specific gene expression is overshadowed by cellular proliferation. In addition, almost every gene over expressed in the short-term AC or UC cultures is down-regulated in the middle and later stage conditions. 143 genes were up-regulated ≥five-fold during this highly proliferative phase, constituting approximately 1.7% of the expressed genes.

The long-term cultures represent the final or senescent phase. In this phase, cells have exhausted their ability to divide, and, especially for AC and UC, the absolute number of differentially expressed genes is noticeably reduced. This may be the result of cells being fully adapted to their culture environment and a consequently reduced burden to biosynthesize. Surprisingly, late BM and DF cultures do not display this same behavior; a large number of genes are differentially expressed in BM-11 and DF-24 relative to AC and UC and the normalized value of 1. AC and UC are distinguishable from BM and DF most notably in the long-term cultures.

The placental stem cell-specific gene list described here is diverse. COL4A1 and COL4A2 are coordinately regulated, and KRT18 and KRT8 also appear to be co-expressed. Eight of the genes encode proteins involved in cell to cell contact, three of which (DSC3, DSG2, and PKP2) are localized to desmosomes, intercellular contact points anchored to intermediate filament cytoskeleton proteins such as keratin 18 and keratin 8. Tight cell-to-cell contact is characteristic of epithelial and endothelial cells and not typically associated with fibroblasts. Table 3 lists 16 genes, of the 46 total, characteristic to epithelial cells. Placental stem cells are generally described as fibroblast-like small spindle-shaped cells. This morphology is typically distinct from BM and DF, especially at lower cell densities. Also of note is the expression pattern of CD200, which is present in AC/UC stem cell and absent in all BM and DF samples. Moreover, CD200 has been shown to be associated with immune tolerance in the placenta during fetal development (see, e.g., Clark et al., *Am. J. Reprod. Immunol.* 50(3):187-195 (2003)).

This subset of genes of 46 genes constitutes a set of molecular biomarkers that distinguishes AC/UC stem cells from bone marrow-derived mesenchymal stem cells or fibroblasts.

5.5 Example 5: Differentiation of Placental Stem Cells

Adherent placental stem cells were differentiated into several different cell lineages. Adherent placental stem cells were isolated from the placenta by physical disruption of placental tissue, and umbilical cord stem cells were obtained by physical disruption of umbilical cord tissue.

Placental stem cells and umbilical cord stem cells were established in a medium containing low concentrations of fetal calf serum and limited growth factors. Flow cytometry analysis showed that placental stem cells typically exhibited a $CD200^+$, $CD105^+$, $CD73^+$, $CD34^-$ $CD45^-$ phenotype at percentages of ≥70%. Placental stem cells were found to differentiate down the adipocyte, chondrocyte and osteocyte lineages.

In an induction medium containing IBMX, insulin, dexamethasone and indomethacin, placental stem cells turned into fat laden adipocytes in 3 to 5 weeks. Under osteogenic induction culture conditions, placental stem cells were found to form bone nodules and have calcium depositions in their extracellular matrix. Chondrogenic differentiation of placental stem cells was performed in micropellets and was confirmed by formation of glycosaminoglycan in the tissue aggregates.

EQUIVALENTS

The compositions and methods disclosed herein are not to be limited in scope by the specific embodiments described herein. Indeed, various modifications of the compositions and methods in addition to those described will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A method of treating an individual having amyotrophic lateral sclerosis (ALS), comprising administering to the individual a therapeutically effective amount of placental stem cells, wherein the therapeutically effective amount is an amount sufficient to detectably reduce or ameliorate one or more symptoms of said ALS, and wherein administration occurs twice per month every one, two, or three months.

2. The method of claim 1, further comprising monitoring one or more of said symptoms in said patient; and administering a second dose of placental stem cells when said one or more symptoms begins to worsen.

3. The method of claim 1, wherein said one or more symptoms comprise difficulty lifting the front part of the foot; difficulty lifting the toes; weakness in one or both legs; weakness in one or both feet; weakness in one or both ankles; hand weakness; hand clumsiness; slurring of speech; trouble swallowing; muscle cramps; twitching in one or both arms; twitching in one or both shoulders and/or twitching of the tongue.

4. The method of claim 1, additionally comprising administering a second therapeutic composition, wherein said second therapeutic composition is riluzole, ceftriaxone, dexpramipexole, creatine+tamoxifen, rasagiline, pioglitazone, arimoclomol, pyrimethamine, trantinoin+pioglitazone, or an antisense molecule or interfering RNA directed against an RNA encoding superoxide dismutase.

5. The method of claim 2, wherein said monitoring comprises monitoring over between 1 and 7 days post-administration.

6. The method of claim 2, wherein said monitoring comprises monitoring over between 7 and 28 days post administration.

7. The method of claim 2, wherein said monitoring comprises monitoring over between 1 and 28 weeks post-administration.

8. The method of claim 1, wherein said placental stem cells are $CD10^+$, $CD34^-$, $CD105^+$ placental stem cells.

9. The method of claim 8, wherein said placental stem cells are additionally $CD200^+$.

10. The method of claim 8, wherein said placental stem cells are additionally $CD45^-$ and $CD90^+$.

11. The method of claim 8, wherein said placental stem cells are additionally $CD80^-$ and $CD86^-$.

12. The method of claim 1 or claim 2, wherein said placental stem cells express CD200 and do not express HLA-G; or express CD73, CD105, and CD200; or express CD200 and OCT-4; or express CD73 and CD105 and do not express HLA-G.

13. The method of claim 8, wherein said placental stem cells are HLA-A,B,$C^+$.

14. The method of claim 1, wherein said placental stem cells are formulated to be administered locally.

15. The method of claim 1, wherein said placental stem cells are formulated to be administered systemically, intravenously, intraarterially, subcutaneously, or intrathecally.

16. The method of claim 1, wherein said therapeutically effective amount comprises at least $1 \times 10^7$ placental stem cells per administration.

17. The method of claim 1, wherein said therapeutically effective amount comprises at least $1 \times 10^8$ placental stem cells per administration.

18. The method of claim 1, wherein said therapeutically effective amount comprises at least $2 \times 10^8$ placental stem cells per administration.

19. The method of claim 1, wherein said therapeutically effective amount comprises at least $1 \times 10^9$ placental stem cells per administration.

20. The method of claim 2, wherein said placental stem cells are $CD10^+$, $CD34^-$, $CD105^+$, and $CD200^+$.

* * * * *